US005939257A

United States Patent [19]
Szasz et al.

[11] Patent Number: 5,939,257
[45] Date of Patent: Aug. 17, 1999

[54] THERMOSTABLE ALKALINE PHOSPHATASES

[75] Inventors: Joseph Szasz, Chardon; Maria Davis, Twinsburg, both of Ohio

[73] Assignee: Amersham Life Science, Inc., Cleveland, Ohio

[21] Appl. No.: 08/738,172

[22] Filed: Oct. 25, 1996

Related U.S. Application Data

[63] Continuation of application No. 08/465,003, Jun. 5, 1995, abandoned, and a continuation-in-part of application No. 08/575,354, Dec. 20, 1995, abandoned, which is a continuation-in-part of application No. 08/240,158, May 10, 1994, abandoned, said application No. 08/465,003, is a continuation-in-part of application No. 08/240,158, May 10, 1994, abandoned, which is a continuation-in-part of application No. 08/229,329, Apr. 18, 1994, abandoned
[60] Provisional application No. 60/005,965, Oct. 27, 1995.

[51] Int. Cl.$^6$ .............................. C12Q 1/68; C12Q 1/42; C12N 9/16; G01N 33/68
[52] U.S. Cl. ............................... 435/6; 435/7.1; 435/7.9; 435/21; 435/196
[58] Field of Search .................................. 435/6, 7.1, 7.9, 435/21, 196

[56] References Cited

FOREIGN PATENT DOCUMENTS

| 9206202 | 4/1992 | WIPO . |
| 9308275 | 4/1993 | WIPO . |
| 9530756 | 11/1995 | WIPO . |
| 9639526 | 12/1996 | WIPO . |

OTHER PUBLICATIONS

Alfredsson et. al., "*Rhodothermus marinus*, gen. nov., sp. nov., a Thermophilic, Halophilic Bacterium from Submarine Hot Springs in Iceland," *J. Gen. Microbiology* 134:299–306 (1988).

Boleznin et al., "An alkaline phosphatase from *Thermus thermophilus* isolation and investigation," *Chemical Abstracts* vol. 107, No. 21, p. 380, abstract No. 193777, Nov. 23, 1987.

Egorova and Loginova, "Selection of a thermophilic Thermus bacterium producing alkaline phosphatase," *Chemical Abstracts* vol. 101, No. 3, p. 482, abstract No. 21989, Jul. 16, 1984.

Hartog et al., "An Alkaline Phosphatase from Thermus sp Strain Rt41A," *Int. J. Biochem.* 24:1657–1660 (1992).

Holgrem et al., "Catalytic Properties and Stability of Three Common Variants of Placental Alkaline Phosphatase," *Medline Asseccion No. 79103184, Biochem Gent.* 16:433–442 (1978).

Huber et al., "*Metallsphaera sedula* gen. and sp. nov. Represents a New Genus of Aerobic, Metal–Mobilizing, Thermoacidophilic Archaebacteria," *System Appl. Microbiol.* 12:38–47 (1989).

Huber et al., "Thermosipho–Africanus New–Genus New–Species Represents a New Genus of Themophilic Eubacterial Within the Thermotogales," *Prikl. Biokhim. Mikrobiol.* 23(4):536–541 (1987), Database Biosis Biosciences Information Service, Philadelphia, PA, US.

Hulett–Cowling and Campbell, "Purification and Properties of an Alkaline Phosphatase of *Bacillus licheniformis*," *Biochemistry* 10:1364–1371 (1971).

Kam et al., "Cloning, Sequencing and Chromosomal Localization of Human Term Placental Alkaline Phosphatase cDNA," *Proc. Natl. Acad. Sci. USA* 82:8715–8719 (1985).

Schaffel et al., "Alkaline Phosphatase from *Bacillus licheniformis*," *Biochem. Biohys. Acta* 526:457–467 (1978).

Tomazic Allen, "Recombinant Bacterial Alkaline Phosphatase as an Immunodiagnostic Enzyme," *Ann. Biol. Clin.* 49(5):287–290 (1991), Database Biosis Biosciences Information Service, Philadelphia, PA, US.

Yeh and Trela, "Purification and Characterization of a Repressible Alkaline Phosphatase from *Thermus aquaticus*," *J. Biol. Chem.* 351:3134–3139 (1976).

Spilliaert et al., "Cloning and sequencing of a *Rhodothermus marinus* gene, *bglA*, coding for a thermostable β–glucanase and its expression in *Escherichia coli*," *European Journal of Biochemistry* 224:923–930 (1994).

M. Nomoto et al., "Purification and Characterization of Extracellular Alkaline Phosphatase From an Alkalophilic Bacterium", *Agric. Biol. Chem.* 52(7): 1643–1647, Jul. 1988.

M. Galka et al., "Alkaline Phosphatase of *Thiobacillus thioparus*. Partial Purification and Properties of the Enzyme", Medline Accession No. 76227786, *Acta Biochim. Pol.* 23(1): 13–26 1976.

M.I. Boleznin et al. "An Alkaline Phosphatase From *Thermus thermophilus*: Isolation and Investigation.", *Prikl. Biokhim. Mikrobiol.* 23(4): 536–541. See Derwent Biotechnol. Absts. 6(23): 99, Abst. No. 87–12567, Nov. 1987.

F. Ducancel et al., "Recombinant Colormetric Antibodies: Constructions and Characterization of a Bifunctional F(ab)2/Alkaline Phosphatase Conjugate Produced in *E. coli*", *Bio/Technology* 11:601–605 May 1993.

W. Wels et al., "Construction, Bacterial Expression and Characterization of a Bifunctional Single–Chain Antibody–Phosphatase Fusion Protein Targeted to the Human ERBB–2 Receptor", *Bio/Technology* 10:1128–1132, Oct. 1992.

A. Carrier et al., "Recombinant Antibody–Alkaline Phosphatase Conjugates for Diagnosis of Human IgGs: Application to Anti–HBsAg Detection", *J. Immunological Meth.* 181:177–186, 1995.

*Primary Examiner*—Rebecca E. Prouty
*Attorney, Agent, or Firm*—Lyon & Lyon LLP

[57] ABSTRACT

Enzymatically active thermostable alkaline phosphatases from *Rhodothermus marinus, Thermus thermophilus*, and *Thermosipho africanus*.

2 Claims, 23 Drawing Sheets

R. marinus Alkaline Phosphatase
4-15% SDS-PAGE

R. marinus Alkaline Phosphatase
Temperature Activity Profile

R. marinus Alkaline Phosphatase
Stability at 65° C

Incubation at 65°C (hours)

R. marinus Alkaline Phosphatase
pH Activity Profile

```
GGGTACCGGAGCGGCCGGGGTTGATGAGCGTGGCGAAGCGCTCGACGATCCGGCCGCCCTGCACACGCACGGCTGCCAGC
TCGATGATCCGATCGGCAGGCCCGGAGCCCGTCGTCTCGGTATCGACGACGACGAACGAAACGGCGTCGAGCTGCATCCC
CTCAGTGGGCTTTCGCCGACGGCTTCCTCCCGCCGGAGGCCGTCTTCGGTCAGGGCTGGCAGGTCGAAACCCATGAGCTT
CGGCCAGTAAGCTGACCGTAGTTCAGTCATTCTCGAAGCTGCCCACCAGCCGATTCGGCGGCACGGATCCGAAGGCGTAC
AGATTGACGTCCACAGCGGTGTGGCCATTCGAGAGTCCAGCCCACCACGGACCCGGCGACCGATCAGCTCGGTAACCACC
TCGGCCCAGGTGTCGGGTTCGGCCGTGGCCTGCGCGACGAGCGCCTGCTCGTCGGCGCGCAGGCTGTCGAGCCCGAGCCA
GGCCTGCAGGAGCGAGTCGGGTCGCTCCGAACGGCGCAGTGCCGGGATAAGCCGTTCGTAGGAAGCCTGCACGCGGGCCA
GCACTTCCGGGTGCCAGTCGTAGACGCCGCGGCCGTCCACGTTGCGCCCCAGCGACAGACCGCCCGTCTCGTGGTCGGCC
ACCGAGACGACGAGCGTCTGTCCGTCGCGGCGGGCAAAGTCGAGCGCCACGGCCACGGCTTCATCGTAAGCCAGCACTTC
GCGGACGTGGGCGGCGGCGTCGTTGGCATGTCCGGCGTGGTCGATGCGGCTGCCCTCCACCATCAGGAAGAAGCCGTCCG
GATCGTCCGCCAGCAGCTCGAGTGCCGCGCGGGTCATCTCGGCCAGCGTAGGGGACCTCTTACCGGGTACGACCGGTCAA
TCTCGTAGGGCAGATGGCTTGGCCCGAACAGTCCCAGCACCGGTCTCCTCACCCCCCGGCGGAAGTCGGCGGCCGTACGC
ACTACCTGGTAGCCCATCGCTTCGGCTTCGCGCAGCAGATTGCGGCCGTCCTGTCTCCGTCCGCCCTCCGCGGTCGGCAG
GAAATAGCTCCAGCCACCCCCCAGCAGCACATCGACGCGTTGCGCCAGCATCTGCGCGGCGATTTCGCTTTCCATGCGCG
CTGCGGCACATGGGCGGCGAAGGCGGCCGGCGTGGCGTGTGAGATCCGGCTGGTCGCCACCAGCCCGGTCGCCATCCCAC
GCGCTTTTGCCGCTTCGAGCAACGTGGCGAGTGGGCGTCCGGCCGTATCGACGGAATCGCGCCGTTGTAGGTCTTGACGC
CGCAGGCATAGGCCGTCGCCCCGGCGAGCCGGAGTCGGTCACCCGGCTGGAGGCCGAAGCAGTACGCACGGCACCGGTCT
GAATGGCATCCAGCGTCAGTTCCTCACGTCCCAGCACGGCCCGGGCATAGTCACGGGCCATCGTGATGCTGGCCGGACCA
CACCCGTCGGCAATCATCAGGATCAGGTTCTTCGGACGCGGCGACTGGGCCCGAGCCCCTTCTCCGACCCCCAACAGCAT
CACCAAAAAACAGCAATATCCAGCGCATTGTCGATTCGCTCCCATCTTGATGAACACGGGCTGTTCAAAGATACGACAGA
TCGGCTTTCATCCACAGCGCCCGGATTATCTACGGAAAGAGCACCATAAAAAAGCCAACCACCCGAACACCTGTCCACCT
TGAGGGCCAACCCGGCCGGGTTGCGACCTCAACGCAGCAGGCCAAACAGGCCGCACAATCACCCCGATCTGTCCGCCAGA
AAATAAACATCCAGCGCACCAGACTTGCATACCGCCGCTTAGCATCACTTTCACCTCGGCAATCCGGCTATCAAGCTTCG
CCTCCACCTCGGCAATCCGGCTGTCGAGCTTCGCCTCCACTTCGGCGATCCGGCCGTCGAGCTTCGCTTCAACCTTGGAG
ATCCGGCCATTAAACTTTGCCTCTACCTCGGCAATTCGGCGGTCAAGCTTCACCTCTACGGCAGCGATGCGTTGTTCCAG
ATGCGACACCTCCTACGCTGAATCCGACGGTCCACGCTTCGCCACCTCCTCCGTGATCGCGTCTGCTCCAGCACGCGCTT
CCACCTCGGTGATGCGATTGTCCAGGCGCTTTTCGGTCTCGGCGACCCGCCGCGCGAAACGCTCCTCTACAATCCCCAGC
AGATTGTTACGCTCGTGATGGGCCGCCTCGTTGAGCAAATTGATGAGCGCCTCGACACCTTCGTCGCCGAGCTTTTCACG
CAAAGCTTTTCACGCAAAACTTTCGGACGGTCAGATTGCCATGAGCGCCTCCACATAGGATAGGCTAAAAGGAAATCGCA
CCTTATTTCTGGAGGTTCCCGTTTTCGTCCAAACCGTCCGGTGTCTCGTTGTCAATTGCCCGGCCAGGTTCGGAGGCTAG
ATTCGAGCTGTCGGGCTAGCCAGGCGCCGTATTGCGGATTGGGCAGGACGATCCAGCGCGTGCCCCACCAGGAGCGATAA
CGCCGGACCAGTGCTCGCCGTGCTTCGGCTCTGGTTTCAGGATCGACATAAAGTCGCCCAGCTGGTCGCCGATCTGGAGC
AGGATGCGATAGCGCTGGCCCAGGATACCCGGCGCGGTTCTTTGTCGGAAGATCCGCATTCGGGCCGCTCGCCACGCGTC
AGGATTACGTCGAGCGTGTACCGGCAGTGGGAAGCCGACGGCCTGCAGGTTACGACGGGTGGCCTCCTCCAGGTCGGCCG
TGCGGTTGGTCACATAAAAGACCTGACGCCGTGCCGGCGCGCCTCCTGTACGAACACGACAGCACCGGGCACAGGTTCGG
CCTGTGCAGCCTGCACCCAGCGCGCCCAGCTCTCCGGCGCAAAAGTCCGGCCCGTCGCAACGAGCCAGGCCTGATAGGGG
CTGTTGTCGAGCACGGTCTCGTCCACGTCCACGATCCACTAGTTCTAGAGCGGCCG
```

FIG. 7

```
TCGCGCGTTTCGGTGATGACGGTGAAAACCTCTGACACATGCAGCTCCCGGAGACGGTCACAGCTTGTCTGTAAGCGGAT
GCCGGGAGCAGACAAGCCCGTCAGGGCGCGTCAGCGGGTGTTGGCGGGTGTCGGGGCTGGCTTAACTATGCGGCATCAGA
GCAGATTGTACTGAGAGTGCACCATATGCGGTGTGAAATACCGCACAGATGCGTAAGGAGAAAATACCGCATCAGGCGCC
ATTCGCCATTCAGGCTGCGCAACTGTTGGGAAGGGCGATCGGTGCGGGCCTCTTCGCTATTACGCCAGCTGGCGAAAGGG
GGATGTGCTGCAAGGCGATTAAGTTGGGTAACGCCAGGGTTTTCCCAGTCACGACGTTGTAAAACGACGGCCAGTGAATT
CGAGCTCGGTACCGAGCGGCCGGGGTTGATGAGCGTGGCGAAGCGCTCGACGATCCGGCCGCCCTGCACACGCACGGCTG
CCAGCTCGATGATCCGATCGGCAGGCCCGGAGCCCGTCGTCTCGGTATCGACGACGACGAACGAAACGGCGTCGAGCTGC
ATCCCCTCAGTGGCTTTCGCCGACGGCTTCCTCCCGCCGGAGCGTCTCGGTCAGGGCTGGCAGGTCGAAACCCATGAGTT
CGGCCAGTAAGCGGCCGAGTTCGTCATTCTCGAAGCTGCCCACCAGCCGTTCGGCGCCGGGTCCGAAGGCGTACAGATTG
ACGTCCACAGCGGTGTGGCCATTCGAGGTCCAGCCCACCACGGCCCGGCGACCGATCAGCTCGGTAACCACCTCGGCCCA
GGTGTCGGGTTCGGCCGTGGCCTGCGCGACGAGCGCCTGCTCGTCGGCGCGCAGGCTGTCGAGCCCGAGCCAGGCCTGCA
GGAGCGAGTCGGGTCGCTCCGAACGGCGCAGTGCCGGGATAAGCCGTTCGTAGGAAGCCTGCACGCGGGCCAGCACTTCC
GGGTGCCAGTCGTAGACGCCGCGGCCGTTCACGTTGCGCCCCAGCGACAGACCGCCCGTCTCGTGGTCGGCCACCGAGAC
GACGAGCGTCTGTCCGTCGCGGCGGGCAAAGTCGAGCGCCACGGCCACGGCTTCATCGTAAGCCAGCACTTCGCGGACGT
GGGCGGCGGCGTCGTTGGCATGTCCGGCGTGGTCGATGCGGCTGCCCTCCACCATCAGGAAGAAGCCGTCCGGATCGTCC
GCCAGCAGCTCGAGTGCCGCGCGGGTCATCTCGGCCAGCGAGGGGACCTCTTCCGGGTCGCGGTCAATCTCGTAGGGCAG
ATGGCTTGGCCCGAACAGTCCCAGCACCGGTCTCCTCACCCCCCGGCGGAAGTCGGCGGCCGTACGCACTACCTGGTAGC
CCATCGCTTCGGCTTCGCGCAGCAGATTGCGGCCGTCCTGTCTCCGTCCGCCCTCCGCGGTCGGCAGGAAATAGCTCCAG
CCACCCCCCAGCAGCACATGGACGCGTTGCGCCAGCATCTGCGCGGCGATTTCGCTTTCCATGGCGCGCTGCGGCACATG
GGCGGCGAAGGCGGCCGGCGTGGCGTGTGAGATCCGGCTGGTCGCCACCAGCCCGGTCGCCATCCCACGCGCTTTTGCCG
CTTCGAGCAACGTGGCGAGTGGGCGTCCGGCCGTATCGACGGCAATCGCGCCGTTGTAGGTCTTGACGCCGCAGGCATAG
GCCGTCGCCCCGGCGGCCGAGTCGGTCACCCGGCTGGAGGCCGAAGCAGTACGCACGGCACCGGTCTGAATGGCATCCAG
CGTCAGTTCCTCACGTCCCAGCACGGCCCGGGCATAGTCACGGGCCATCGTGATGCTGGCCGGACCACACCCGTCGGCAA
TCATCAGGATCAGGTTCTTCGGACGCGGCGACTGGGCCCGAGCCCCTTCTCCGACCCCCAACAGCATCACCAAAAACAGC
AATATCCAGCGCATTGTGCATCGCTCCATCTGATGAACACGGGCTGTTCAAAGATACGACAGATCGGCTTTCATCCACAG
CCCCGGATACTACGGAAAGAGCACCATAAAAAAGCCAACCACCCGAACACCTGTCCACCTTGAGGGCCAACCCGGCCGGG
TTGCGACCTCAACGCAGCAGCGCAAACAGCGCCACAATCACCCCGATCTGTCCCGCCCAGAAAATAAACATCCAGCGCAC
CAGACTTGCATACCGCTCGCTTAGCATCACTTTCACCTCGGCAATCCGGCTATCAAGCTTGGCGTAATCATGGTCATAGC
TGTTTCCTGTGTGAAATTGTTATCCGCTCACAATTCCACACAACATACGAGCCGGAAGCATAAAGTGTAAAGCCTGGGGT
GCCTAATGAGTGAGCTAACTCACATTAATTGCGTTGCGCTCACTGCCCGCTTTCCAGTCGGGAAACCTGTCGTGCCAGCT
GCATTAATGAATCGGCCAACGCGCGGGGAGAGGCGGTTTGCGTATTGGGCGCTCTTCCGCTTCCTCGCTCACTGACTCGC
TGCGCTCGGTCGTTCGGCTGCGGCGAGCGGTATCAGCTCACTCAAAGGCGGTAATACGGTTATCCACAGAATCAGGGGAT
AACGCAGGAAAGAACATGTGAGCAAAAGGCCAGCAAAAGGCCAGGAACCGTAAAAAGGCCGCGTTGCTGGCGTTTTTCCA
TAGGCTCCGCCCCCCTGACGAGCATCACAAAAATCGACGCTCAAGTCAGAGGTGGCGAAACCCGACAGGACTATAAAGAT
ACCAGGCGTTTCCCCCTGGAAGCTCCCTCGTGCGCTCTCCTGTTCCGACCCTGCCGCTTACCGGATACCTGTCCGCCTTT
CTCCCTTCGGGAAGCGTGGCGCTTTCTCAATGCTCACGCTGTAGGTATCTCAGTTCGGTGTAGGTCGTTCGCTCCAAGCT
GGGCTGTGTGCACGAACCCCCCGTTCAGCCCGACCGCTGCGCCTTATCCGGTAACTATCGTCTTGAGTCCAACCCGGTAA
GACACGACTTATCGCCACTGGCAGCAGCCACTGGTAACAGGATTAGCAGAGCGAGGTATGTAGGCGGTGCTACAGAGTTC
TTGAAGTGGTGGCCTAACTACGGCTACACTAGAAGGACAGTATTTGGTATCTGCGCTCTGCTGAAGCCAGTTACCTTCGG
AAAAAGAGTTGGTAGCTCTTGATCCGGCAAACAAACCACCGCTGGTAGCGGTGGTTTTTTTGTTTGCAAGCAGCAGATTA
CGCGCAGAAAAAAAGGATCTCAAGAAGATCCTTTGATCTTTTCTACGGGGTCTGACGCTCAGTGGAACGAAAACTCACGT
TAAGGGATTTTGGTCATGAGATTATCAAAAAGGATCTTCACCTAGATCCTTTTAAATTAAAAATGAAGTTTTAAATCAAT
CTAAAGTATATATGAGTAAACTTGGTCTGACAGTTACCAATGCTTAATCAGTGAGGCACCTATCTCAGCGATCTGTCTAT
TTCGTTCATCCATAGTTGCCTGACTCCCCGTCGTGTAGATAACTACGATACGGGAGGGCTTACCATCTGGCCCCAGTGCT
GCAATGATACCGCGAGACCCACGCTCACCGGCTCCAGATTTATCAGCAATAAACCAGCCAGCCGGAAGGGCCGAGCGCAG
AAGTGGTCCTGCAACTTTATCCGCCTCCATCCAGTCTATTAATTGTTGCCGGGAAGCTAGAGTAAGTAGTTCGCCAGTTA
ATAGTTTGCGCAACGTTGTTGCCATTGCTACAGGCATCGTGGTGTCACGCTCGTCGTTTGGTATGGCTTCATTCAGCTCC
GGTTCCCAACGATCAAGGCGAGTTACATGATCCCCCATGTTGTGCAAAAAAGCGGTTAGCTCCTTCGGTCCTCCGATCGT
```

*FIG. 8A*

```
TGTCAGAAGTAAGTTGGCCGCAGTGTTATCACTCATGGTTATGGCAGCACTGCATAATTCTCTTACTGTCATGCCATCCG
TAAGATGCTTTTCTGTGACTGGTGAGTACTCAACCAAGTCATTCTGAGAATAGTGTATGCGGCGACCGAGTTGCTCTTGC
CCGGCGTCAATACGGGATAATACCGCGCCACATAGCAGAACTTTAAAAGTGCTCATCATTGGAAAACGTTCTTCGGGGCG
AAAACTCTCAAGGATCTTACCGCTGTTGAGATCCAGTTCGATGTAACCCACTCGTGCACCCAACTGATCTTCAGCATCTT
TTACTTTCACCAGCGTTTCTGGGTGAGCAAAAACAGGAAGGCAAAATGCCGCAAAAAAGGGAATAAGGGCGACACGGAAA
TGTTGAATACTCATACTCTTCCTTTTTCAATATTATTGAAGCATTTATCAGGGTTATTGTCTCATGAGCGGATACATATT
TGAATGTATTTAGAAAAATAAACAAATAGGGGTTCCGCGCACATTTCCCCGAAAAGTGCCACCTGACGTCTAAGAAACCA
TTATTATCATGACATTAACCTATAAAAATAGGCGTATCACGAGGCCCTTTCGTC
```

FIG. 8B

```
1/1                                              31/11
ATG CGC TGG ATA TTG CTG TTT TTG GTG ATG CTG TTG GGG GTC GGA GAA GGG GCT CGG GCC
 M   R   W   I   L   L   F   L   V   M   L   L   G   V   G   E   G   A   R   A
61/21                                            91/31
CAG TCG CCG CGT CCG AAG AAC CTG ATC CTG ATG ATT GCC GAC GGG TGT GGT CCG GCC AGC
 Q   S   P   R   P   K   N   L   I   L   M   I   A   D   G   C   G   P   A   S
121/41                                           151/51
ATC ACG ATG GCC CGT GAC TAT GCC CGG GCC GTG CTG GGA CGT GAG GAA CTG ACG CTG GAT
 I   T   M   A   R   D   Y   A   R   A   V   L   G   R   E   E   L   T   L   D
181/61                                           211/71
GCC ATT CAG ACC GGT GCC GTG CGT ACT GCT TCG GCC TCC AGC CGG GTG ACC GAC TCG GCC
 A   I   Q   T   G   A   V   R   T   A   S   A   S   S   R   V   T   D   S   A
241/81                                           271/91
GCC GGG GCG ACG GCC TAT GCC TGC GGC GTC AAG ACC TAC AAC GGC GCG ATT GCC GTC GAT
 A   G   A   T   A   Y   A   C   G   V   K   T   Y   N   G   A   I   A   V   D
301/101                                          331/111
ACG GCC GGA CGC CCA CTC GCC ACG TTG CTC GAA GCG GCA AAA GCG CGT GGG ATG GCG ACC
 T   A   G   R   P   L   A   T   L   L   E   A   A   K   A   R   G   M   A   T
361/121                                          391/131
GGG CTG GTG GCG ACC AGC CGG ATC TCA CAC GCC ACG CCG GCC GCC TTC GCC GCC CAT GTG
 G   L   V   A   T   S   R   I   S   H   A   T   P   A   A   F   A   A   H   V
421/141                                          451/151
CCG CAG CGC GCC ATG GAA AGC GAA ATC GCC GCG CAG ATG CTG GCG CAA CGC GTC CAT GTG
 P   Q   R   A   M   E   S   E   I   A   A   Q   M   L   A   Q   R   V   H   V
481/161                                          511/171
CTG CTG GGG GGT GGC TGG AGC TAT TTC CTG CCG ACC GCG GAG GGC GGA CGG AGA CAG GAC
 L   L   G   G   G   W   S   Y   F   L   P   T   A   E   G   G   R   R   Q   D
541/181                                          571/191
GGC CGC AAT CTG CTG CGC GAA GCC GAA GCG ATG GGC TAC CAG GTA GTG CGT ACG GCC GCC
 G   R   N   L   L   R   E   A   E   A   M   G   Y   Q   V   V   R   T   A   A
601/201                                          631/211
GAC TTC CGC CGG GGG GTG AGG AGA CCG GTG CTG GGA CTG TTC GGG CCA AGC CAT CTG CCC
 D   F   R   R   G   V   R   R   P   V   L   G   L   F   G   P   S   H   L   P
661/221                                          691/231
TAC GAG ATT GAC CGC GAC CCG GAA GAG GTC CCC TCG CTG GCC GAG ATG ACC CGC GCG GCA
 Y   E   I   D   R   D   P   E   E   V   P   S   L   A   E   M   T   R   A   A
721/241                                          751/251
CTC GAG CTG CTG GCG GAC GAT CCG GAC GGC TTC TTC CTG ATG GTG GAG GGC AGC CGC ATC
 L   E   L   L   A   D   D   P   D   G   F   F   L   M   V   E   G   S   R   I
781/261                                          811/271
GAC CAC GCC GGA CAT GCC AAC GAC GCC GCC GCC CAC GTC CGC GAA GTG CTG GCT TAC GAT
 D   H   A   G   H   A   N   D   A   A   A   H   V   R   E   V   L   A   Y   D
841/281                                          871/291
GAA GCC GTG GCC GTG GCG CTC GAC TTT GCC CGC CGC GAC GGA CAG ACG CTC GTC GTC TCG
 E   A   V   A   V   A   L   D   F   A   R   R   D   G   Q   T   L   V   V   S
901/301                                          931/311
GTG GCC GAC CAC GAG ACG GGC GGT CTG TCG CTG GGG CGC AAC GTG AAC GGC CGC GGC GTC
 V   A   D   H   E   T   G   G   L   S   L   G   R   N   V   N   G   R   G   V
961/321                                          991/331
```

*FIG. 9A*

```
TAC GAC TGG CAC CCG GAA GTG CTG GCC CGC GTG CAG GCT TCC TAC GAA CGG CTT ATC CCG
 Y   D   W   H   P   E   V   L   A   R   V   Q   A   S   Y   E   R   L   I   P
1021/341                                1051/351
GCA CTG CGC CGT TCG GAG CGA CCC GAC TCG CTC CTG CAG GCC TGG CTC GGG CTC GAC AGC
 A   L   R   R   S   E   R   P   D   S   L   L   Q   A   W   L   G   L   D   S
1081/361                                1111/371
CTG CGC GCC GAC GAG CAG GCG CTC GTC GCG CAG GCC ACG GCC GAA CCC GAC ACC TGG GCC
 L   R   A   D   E   Q   A   L   V   A   Q   A   T   A   E   P   D   T   W   A
1141/381                                1171/391
GAG GTG GTT ACC GAG CTG ATC GGT CGC CGG GCC GTG GTG GGC TGG ACC TCG AAT GGC CAC
 E   V   V   T   E   L   I   G   R   R   A   V   V   G   W   T   S   N   G   H
1201/401                                1231/411
ACC GCT GTG GAC GTC AAT CTG TAC GCC TTC GGA CCC GGC GCC GAA CGG CTG GTG GGC AGC
 T   A   V   D   V   N   L   Y   A   F   G   P   G   A   E   R   L   V   G   S
1261/421                                1291/431
TTC GAG AAT GAC GAA CTC GGC CGC TTA CTG GCC GAA CTC ATG GGT TTC GAC CTG CCA GCC
 F   E   N   D   E   L   G   R   L   L   A   E   L   M   G   F   D   L   P   A
1321/441                                1351/451
CTG ACC GAG ACG CTC CGG CGG GAG GAA GCC GTC GGC GAA AGC CAC TGA
 L   T   E   T   L   R   R   E   E   A   V   G   E   S   H   *
```

FIG. 9B

Tth Alkaline Phosphatase pH Activity Profile

Tth Alkaline Phosphatase
Activity vs Ionic Strength

ASSAY: 10mM CAPS pH 11.0
XmM NaCl
6mM pNPP

Tth Alkaline Phosphatase Stability at 70°

♦— Tris pH + 15% glycerol
▣— Tris pH 8.0
□— CAPS PH 11.0 + 15% glycerol

ASSAY: 100mM CAPS pH 11.0
15% glycerol
6mM pNPP
37°C

Tth Alkaline Phosphatase
NH$_2$-terminal Amino Acid Sequence

MET-VAL-(LEU*)-PRO-VAL-LEU-TYR

* MINOR COMPONENT

Deduced Nucleotide Sequence

A DEGENERATED 17bp DNA PROBE, INCORPORATING THE CODON BIAS OF Tth GENES:
ATG(GC)T(GC)CC(GC)GT(GC)CT(GCT)TA

*FIG. 16.*

Tth Alkaline Phosphatase
NH$_2$-terminal Amino Acid Sequence

VAL-LYS-ASN-VAL-ILE-TYR-MET-ILE-GLY-
ASP-GLY-MET-GLY-ILE(LYS*)-ASN-

* MINOR COMPONENT

*FIG. 21.*

Tsa Alkaline Phosphatase pH Activity Profile

ASSAY: 100mM glycine-NaOH; pH 8.2-9.9
100mm CAPS; pH 10.2-11.3
6mM p-nitrophenyl phosphate
37°C Tsa Alkaline Phosphatase
Temperature Activity Profile ASSAY: 100mM glycine-NaOH; pH 10.6
1mM Mg++, 1mM Zn++, 6mM pNPP Tsa Alkaline Phosphatase
Stability at 65° C STABILITY BUFFER: 25mM Tris pH 8.0
 360 mM NaCl
 10% glycerol
 1mM EDTA
 1mM DTT ASSAY: 100mM glycine-NaOH pH 10.6
 6mM p-nitrophenyl phosphate
 1mM Mg++
 1mM Zn++
 37°C

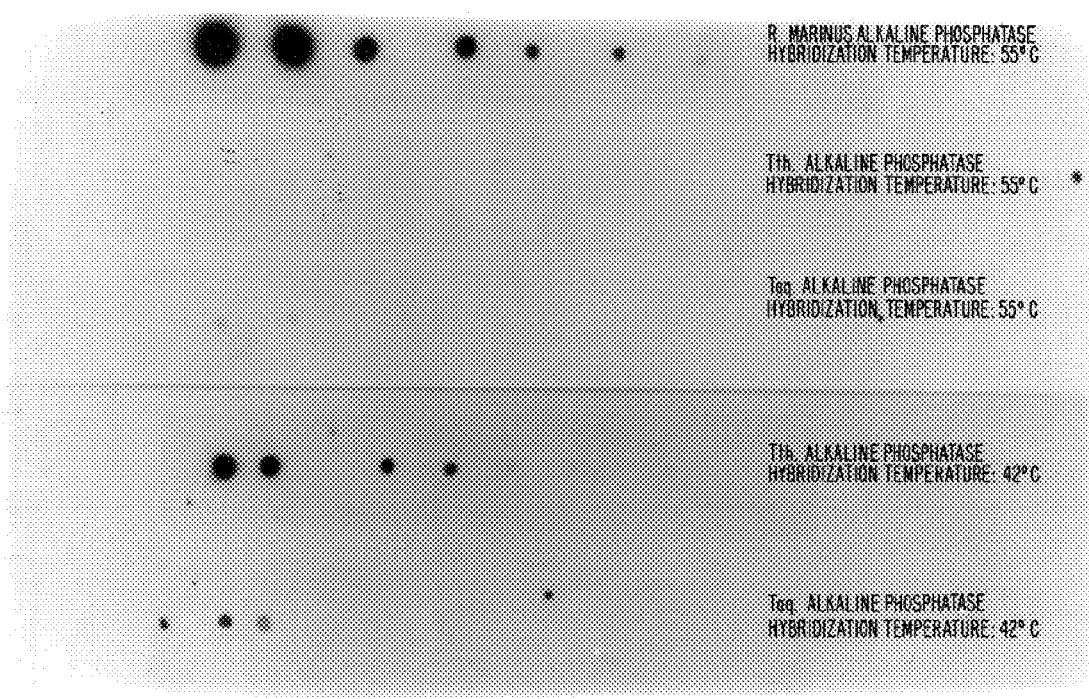
FIG. 22. Lambda DNA / HindIII Dot Blot

THERMOSTABLE ALKALINE PHOSPHATASES

This application claims priority to Provisional Application, Szasz et al., U.S. Ser. No. 60/005,965 filed Oct. 27, 1995, entitled "Thermostable Alkaline Phosphatase of Rhodothermus Marinus". This application is also a continuation of U.S. Ser. No. 08/465,003, filed Jun. 5, 1995, now abandoned which is a continuation-in-part of Davis et al., U.S. Ser. No. 08/240,158, filed May 10, 1994 entitled "Thermostable Alkaline Phosphatase of Thermus Thermophilus", now abandoned, which is a continuation-in-part of Davis et al., U.S. Ser. No. 08/229,329, filed Apr. 18, 1994, entitled "Thermostable Alkaline Phosphatase of Thermosipho Africanus", now abandoned. This application is also a continuation-in-part of U.S. Ser. No. 08/575,354, filed Dec. 20, 1995, now abandoned, which is a continuation-in-part of "Thermostable Alkaline Phosphatase of Thermus Thermophilus," filed May 10, 1994, by Davis and Szasz and assigned U.S. Ser. No. 08/240,158, now abandoned. The above-captioned applications are incorporated by reference herein, including drawings.

BACKGROUND OF THE INVENTION

Alkaline phosphatases are commonly used in routine biochemical procedures to remove phosphate groups from the termini of nucleic acid molecules. For example, calf intestinal alkaline phosphatase is a heat labile enzyme which is used to remove such phosphate groups, and then is inactivated by exposure to a high temperature. This thermal instability is advantageous because the alkaline phosphatase need not be removed from the reaction mixture prior to subsequent manipulations.

Alkaline phosphatase is also used as a non-radioactive marker for the detection of specific protein or DNA targets. It is conjugated to proteins or DNA oligonucleotides to aid in detection of such targets. Enzyme thermostability is desirable for use in labelling DNA molecules, especially those larger than 50 bp, and may be useful in other applications for increased stability of the enzyme during storage.

The following is a discussion of relevant art, none of which is admitted to be prior art to the present invention.

Alkaline phosphatases from various thermophilic and other organisms are known: Yeh and Trela (1976) "Purification and Characterization of a Repressible Alkaline Phosphatase from *Thermus aquaticus*" *J. Biol. Chem.* 251:3134–3139; Hartog and Daniel (1992) "An Alkaline Phosphatase from Thermus sp Strain Rt41A" *Int. J. Biochem.* 24:1657–1660; Schaffel and Hulett (1978) "Alkaline Phosphatase from *Bacillus licheniformis*" *Biochimica et Biophysica Acta* 526:457–467; Hulett-Cowling and Campbell (1971) "Purification and Properties of an Alkaline Phosphatase of *Bacillus licheniformis*" *Biochem.* 10: 1364–1371.

SUMMARY OF THE INVENTION

Applicant has isolated and purified novel alkaline phosphatases from three prokaryotes; the thermophilic species *Rhodothermus marinus, Thermosipho africanus*, and *Thermus thermophilus*. These enzymes have high pH optimums of (~10.8, ~11, 13 or greater, respectively) and are thermostable, retaining 50–60% of their activity even after 24 hours incubation at 65° C. These enzymes are also tolerant of other denaturing conditions, including overnight incubation in 6M urea at 65° C. The higher pH optimum of these enzyme is a significant advantage. This high pH optimum, and thus stability at high pH, enhances the use of these enzymes in non-radioactive detection systems, for example, when the enzymes are used with streptavidin. In addition, the high pH optimum of the enzymes makes them suitable for use with dioxetane substrates which undergo rapid conversion to the luminescent form at alkaline pH. The thermostability of the alkaline phosphatase is also advantageous in that following direct cross-linking of the enzyme to nucleic acid probes, it allows hybridization and subsequent washes of such labelled probes under stringent conditions, that is, at elevated temperatures without significant loss of enzyme activity.

Thus, in a first aspect the invention features an enzymatically active portion of the thermostable alkaline phosphatase present in *Rhodothermus marinus* having a pH optimum greater than 10.5, e.g. 10.8, which is also resistant to a temperature of at least 65° C. (i.e., maintains at least 10% of its activity at this temperature).

By phosphatase is simply meant a protein or fragment thereof having an activity which removes a phosphate group from a molecule, such as a DNA molecule or another molecule, such as p-nitrophenyl phosphate (pNPP). An "alkaline phosphatasen" is one which is active at a pH greater than 7, and in the present invention has a pH optimum greater than 10.0 using the conditions listed below. Those skilled in the art recognize that pH optimum is dependant on buffer conditions and substrate concentration.

By "thermostable" is meant that the enzyme maintains at least 10% of its activity after heating at 65° C. for one hour or longer, preferably for 5 or 10 hours.

The invention also encompasses other enzymatically active thermostable alkaline phosphatases which have at least 75% homology to the enzymatically active portion of the alkaline phosphatase of *Rhodothermus marinus* shown in FIGS. 9A & B (SEQ. ID. NO. 4). By 75% homology is meant that the thermostable alkaline phosphatase can have an amino acid sequence which differs from that of *Rhodothermus marinus* by as much as 25% and still maintain substantially the same enzymatic activity (i.e., the ability to remove a phosphate group from a molecule) as the enzymatically active portion of the alkaline phosphatase of *Rhodothermus marinus*. Such differences include conservative changes, additions, deletions, and substitutions other than degenerate codons. In preferred embodiments, the amino acid sequence of the alkaline phosphatase includes less than 10 conservative amino acid changes or less than 10 additional amino acids compared to the enzymatically active portion of the alkaline phosphatase of *Rhodothermus marinus*. By substantially the same enzymatic efficiency is meant at least 50% of the activity of the enzymatically active portion of the thermostable alkaline phosphatase of *Rhodothermus marinus*.

Using standard techniques the enzymes of this invention can be readily cloned, for example, by microsequencing of the protein or fragments thereof, preparation of oligonucleotides useful as probes for a library of clones generated from the nucleic acid of a desired organism, e.g., *Rhodothermus marinus* and screening of that library with such probes to isolate fragments of DNA encoding the protein. Alternatively, an antibody to the protein may be produced and an expression library screened to determine which clone expresses an antigenic determinant recognized by that antibody. Other standard techniques are well known to those of ordinary skill in the art to isolate such genes encoding the claimed proteins. Such genes encode recombinant alkaline phosphatase.

Thus, in a second aspect the invention features recombinant alkaline phosphatase having the above properties, and cells encoding nucleic acid including such recombinant DNA. Equivalent genes encoding such phosphatases can be cloned using standard methodology.

Applicant has also isolated and purified a novel alkaline phosphatase from the thermophilic species *Thermus thermophilus*. This enzyme has an extremely high pH optimum (pH13 or greater), and is thermostable, retaining at least 50% of its activity even after 24 hours incubation at 65° C.

Thus, in a third aspect the invention features an enzymatically active portion of the thermostable alkaline phosphatase present in *Thermus thermophilus* (Tth) having a pH optimum greater than 10.5, preferably an optimum at a pH equal to or greater than 11, which is also resistant to a temperature of at least 65° C. (i.e., maintains at least 10% of its activity at this temperature). Such activity may be measured in a variety of buffers, e.g., CAPS, TRIS, TAPS, Glycine, Na phosphate and KCl—NaOH, in the presence or absence of glycerol and divalent cations (see, FIG. 10). As will be shown below, the activity of the phosphatases of this invention will vary dependent on such conditions. Thus, an alkaline phosphatase from *Thermus thermophilus* preferably has its activity optimum measured in the presence of glycerol in 100 mM CAPS, e.g., in the presence of calcium ions.

Using standard techniques the enzyme described below can be readily cloned, for example, by microsequencing of the protein or fragments thereof, preparation of oligonucleotides useful as probes for a library of clones generated from the nucleic acid of a desired organism, e.g., *Thermus thermophilus*, and screening of that library with such probes to isolate fragments of DNA encoding the protein. One such probe has been identified by determining the amino-terminal sequence of the native protein (SEQ ID NO. 6), and this is given in FIG. 16. From this amino acid sequence, a degenerate oligonucleotide probe can be designed (SEQ ID NO. 7) (see FIG. 16). The known codon bias of *Thermus thermophilus* could be incorporated into the probe design, to increase the specificity of the probe by decreasing the degeneracy of the oligonucleotide. Alternatively, an antibody to the native protein or a peptide antibody directed against the amino terminus may be produced and an expression library screened to determine which clone expresses an antigenic determinant recognized by that antibody. The degenerate oligonucleotide probe could alternatively be used as the 5' end primer in a PCR reaction utilizing total genomic DNA from Tth as a template. For a 3' primer, one could design another oligonucleotide either from sequences conserved among bacterial alkaline phosphatases, or from an internal peptide sequence derived from Tth alkaline phosphatase. Other standard techniques are well known to those of ordinary skill in the art to isolate such genes encoding the claimed proteins. Such genes encode recombinant alkaline phosphatase.

The recombinant DNA encoding the Tth alkaline phosphatase is distinct from those previously isolated. For example, Cam et al., 82 *Proc. Natl. Acad. Sci, USA* 8715–8719, December 1985 describes the cloning of a human placental alkaline phosphatase. This enzyme has a different subunit size and N-terminal sequence than that of the Tth alkaline phosphatase. As evidenced by Cam et al. standard procedures can be used to equivalently isolate the present Tth alkaline phosphatase. The enzyme is also distinct from that present in *Thermus aquaticus* and can be distinguished by migration properties on SDS polyacrylamide gels. The alkaline phosphatase described herein has a subunit size of approximately 51,000 Daltons.

Thus, in a fourth aspect the invention features recombinant alkaline phosphatase having the above properties, and cells encoding nucleic acid including such recombinant DNA. Equivalent genes encoding such phosphatases can be cloned using standard methodology. Such recombinant Tth corresponds in amino acid sequence to the amino acid sequence of the enzymatic portion of naturally occurring Tth, or the whole of such a natural Tth.

Applicant has also isolated and purified a novel alkaline phosphatase from the thermophilic species *Thermosipho africanus*. This enzyme has an extremely high pH optimum (around pH 11), and is thermostable, retaining 50% of its activity even after 24 hours incubation at 65° C.

Thus, in a fifth aspect the invention features an enzymatically active portion of the thermostable alkaline phosphatase present in *Thermosipho africanus* (Tsa) having a pH optimum greater than 10.5, preferably an optimum at pH 11, which is also resistant to a temperature of at least 65° C. (i.e., maintains at least 10% of its activity at this temperature).

Using standard techniques the enzyme described below can be readily cloned, for example, by microsequencing of the protein or fragments thereof, preparation of oligonucleotides useful as probes for a library of clones generated from the nucleic acid of a desired organism, e.g., *Thermosipho africanus*, and screening of that library with such probes to isolate fragments of DNA encoding the protein. Alternatively, an antibody to the protein may be produced and an expression library screened to determine which clone expresses an antigenic determinant recognized by that antibody. Other standard techniques are well known to those of ordinary skill in the art to isolate such genes encoding the claimed proteins. Such genes encode recombinant alkaline phosphatase.

Thus, in a sixth aspect the invention features recombinant alkaline phosphatase having the above properties, and cells encoding nucleic acid including such recombinant DNA. Equivalent genes encoding such phosphatases can be cloned using standard methodology.

The alkaline phosphatase of *Thermosipho africanus* (Tsa) is distinct from that present in *Thermus aquaticus* (Taq) and *Thermus thermophilus* (Tth). As shown in the data presented below on an SDS PAGE gel (See FIG. 20) the subunit size of the Tsa alkaline phosphatase (apparent molecular weight approximately 47,000 Daltons) is different from the subunit sizes of alkaline phosphatase from both Taq and Tth with apparent molecular weights of about 51,000 Daltons each.

While applicant provides several examples of alkaline phosphatases of the present invention, those in the art armed with the fact that an alkaline phosphatase having a pH optimum of greater than 10.5, about 11, or greater than 11, exists in nature and can be isolated can now readily screen cellular extracts to determine the presence of such an activity, and can use standard methodology as described herein to isolate and purify other such an enzymatic portions.

In the present invention, the enzymes are preferably provided in a purified form, that is, it is isolated from the environment in which it naturally occurs. Generally, such an environment is within a bacterial cell and the protein is isolated from the cell wall and/or membranes of that cell such that it is enriched at least 10- or 100-fold compared to its presence in the cell. More preferably, it is enriched 1000- or 10,000- or more fold such that it is an essentially homogeneous preparation, that is, it is the predominant species of protein in a preparation. Even more preferably, the protein is the only species, that is, it represents at least 95% of the proteinaceous material in a sample. Such a protein may be prepared from the bacterial cells in which it naturally occurs, or may be prepared using standard recombinant DNA methodology to cause high levels of expression of the protein in a bacterium or other cell in which it does not naturally occur, e.g., *E. coli*. A crude extract of such recombinant protein is included within the definition of purified protein.

In a seventh aspect, the invention features a method for use of thermostable alkaline phosphatases in labelling of protein or nucleic acid, and in various molecular biology techniques. Thus, the enzymes of the present invention may be used in standard labelling reactions and in diagnostic assays. They may be also used in molecular biology techniques in which removal of a phosphate group is desired.

In preferred embodiments the thermostable alkaline phosphatase is of prokaryotic origin; the alkaline phosphatase is from *Rhodothermus marinus*; the alkaline phosphatase is from *Thermus thermophilus*; the alkaline phosphatase is from *Thermosipho africanus*.

Other features and advantages of the invention will be apparent from the following description of the preferred embodiments thereof, and from the claims.

DESCRIPTION OF THE PERFERRED EMBODIMENT

The drawings will first briefly be described.
Drawings

FIG. 1 is a reproduction of a SDS-PAGE gel of purified *Rhodothermus marinus* alkaline phosphatase. Lane 1 represents molecular weight markers. Lanes 2, 3, 4, and 5 represent 0.4, 0.8, 1.6 and 3.2 ug of purified protein, respectively.

FIG. 2 is a graphical representation of the temperature activity profile of purified *Rhodothermus marinus* alkaline phosphatase. Temperature is presented on the x-axis. Specific activity (u/mg) is presented on the y-axis.

FIG. 3 is a graphical representation of the stability of purified *Rhodothermus marinus* alkaline phosphatase at 65° C. Incubation at 65° C. (hours) is presented on the x-axis. Percent initial activity is presented on the y-axis.

FIG. 4 is a graphical representation of the pH activity profile of purified *Rhodothermus marinus* alkaline phosphatase. Open squares represent enzyme activity assayed in 0.1M CAPS, 1 mM $MgCl_2$ and 6 mM pNPP. Solid diamonds represent enzyme activity assayed in 0.1M each of ethanolamine, diethanolamine, triethanolamine, 1mM $MgCl_2$ and 6 mM pNPP. On the x-axis pH is presented. Specific activity (u/mg) is presented on the y-axis.

FIG. 5 is a representation of non-isotopic detection of various amounts (0.01 ng, 0.05 ng, 0.1 ng, 0.5 ng, 1 ng, 5 ng, 10 ng) of dot blotted DNA with *Rhodothermus marinus* alkaline phosphatase.

FIG. 6 represents a Southern Blot of human genomic DNA probed with an N-ras DNA fragment labelled with cloned *Rhodothermus marinus* alkaline phosphatase. Four amounts of total DNA were loaded: 1.0, 0.5, 0.2, 0.1 μg. Target DNA is equivalent to 0.5, 0.25, 0.1, 0.05 pg.

FIG. 7 represents a sequence of genomic DNA from *Rhodothermus marinus*, containing the gene for alkaline phosphatase and flanking regions (SEQ. ID. NO. 1).

FIGS. 8A & B represents a sequence of plasmid pCRM1.8, containing a 1.8 kb segment of genomic DNA containing alkaline phosphatase and flanking sequences from *Rhodothermus marinus*, cloned into pUC19 (SEQ. ID. NO. 2).

FIGS. 9A & B represents a presumptive full-length protein sequence (455 amino acids) of Rma alkaline phosphatase (SEQ. ID. NO. 4) and the corresponding nucleic acid sequence (1368 bp) (SEQ. ID. NO. 3). The first 20 amino acids are presumed to function as a signal sequence in *E. coli*. The underlined portion of the amino acid sequence has been verified by protein sequencing of cloned enzyme isolated from *E. coli*.

FIG. 16 is a partial amino acid sequence of Tth alkaline phosphatase derived from the amino terminus of the protein (SEQ ID NO. 6). The corresponding oligonucleotides to this sequence are also shown (SEQ ID NO. 7).

FIG. 21 is the Tsa alkaline phosphatase $NH_2$-terminal amino acid sequence (SEQ ID NO. 5).

FIG. 22 represents a dot blot of various amounts of lambda DNA detected with *Rhodothermus marinus* alkaline phosphatase, *Thermus thermophilus* alkaline phosphatase, and *Thermus aquaticus* alkaline phosphatase.

Figure 1:
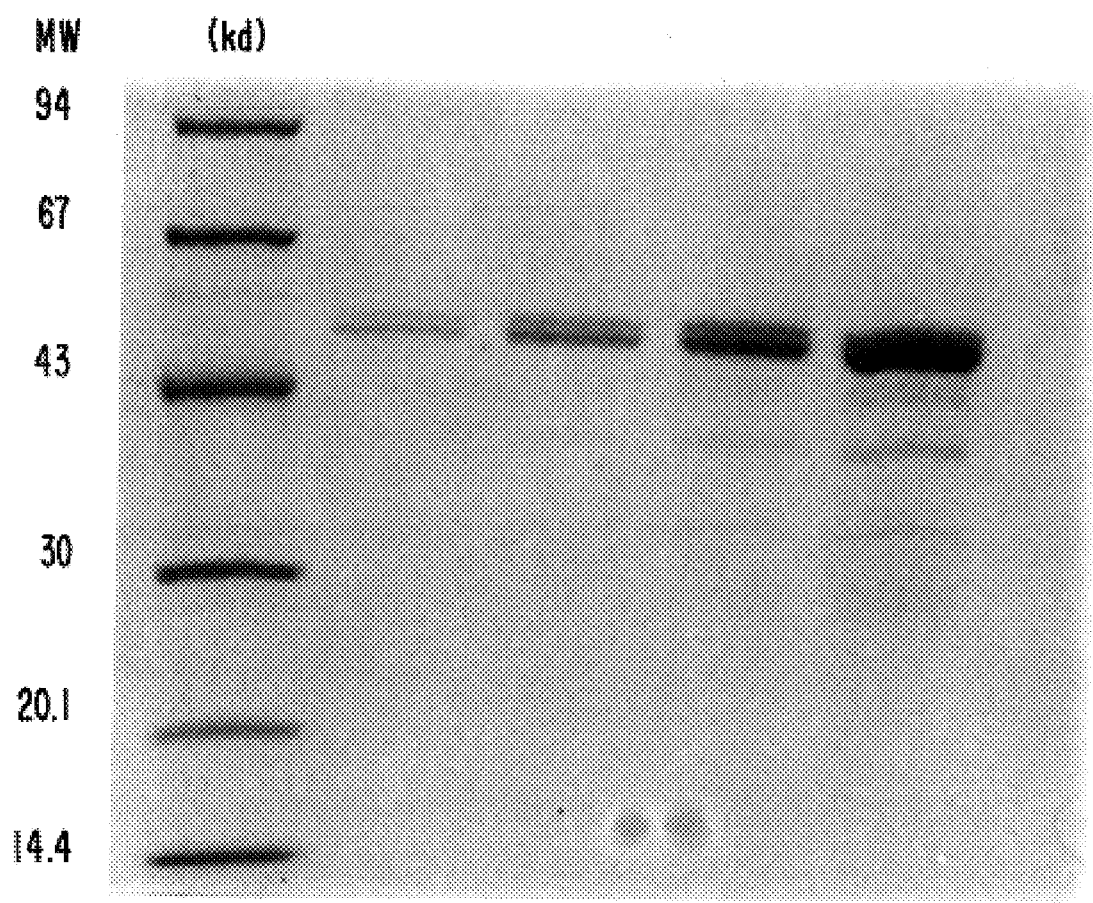

The following are examples of the alkaline phosphatases of the present invention. These are not limiting in the invention.
Rhodothermus Marinus

EXAMPLE 1

Isolation and Characterization of Alkaline Phosphatase from *Rhodothermus Marinus*
Culture conditions:

*Rhodothermus marinus*, strain ATCC 43812 was grown under aerobic conditions at 65° C. as described by Alfredsson et. al.(1988) "*Rhodothermus marinus*, gen. nov., sp. nov., a Thermophilic, Halophilic Bacterium from Submarine Hot Springs in Iceland" *J. Gen. Microbiology* 134, 299–306. Cells were harvested by continual flow centrifugation and stored at −80° C.
Activity assay:

Alkaline phosphatase activity was monitored spectrophotometrically at 405 nm by following the conversion of p-nitrophenylphosphate (pNPP) to p-nitrophenol. One unit is defined as the amount of enzyme required to release one micromole of p-nitrophenol in one minute. All assays were performed in 100 mM CAPS (3-(cyclohexylamino)-1-propanesulfonic acid) pH 10, 15% glycerol, 1 mM $MgCl_2$ and 6 mM PNPP at 37° C. unless otherwise specified.

Purification:

Frozen cells (33 g) were resuspended in 25 mM Tris-HCl pH 7.4, 50 mM NaCl, 1 mM $MgCl_2$ and 0.1% Triton X-100 (100 ml final volume) and lysed by sonication. The lysate was cleared of cellular debris by centrifugation, supplemented to a final NaCl concentration of 350 mM and chromatographed on DE 52 anionic exchange resin (Whatman; 4 g resin per g cells) equilibrated in 25 mM Tris-HCl pH 7.4 and 350 mM NaCl. The majority of alkaline phosphatase activity appeared in the flow through which was diluted in 25 mM Tris-HCl pH 7.4 to lower the salt concentration to 100 mM. The diluted flow through was applied to a column of Heparin Sepharose CL-6B resin (Pharmacia) equilibrated in 25 mM Tris-HCl pH 7.4 and 100 mM NaCl. Alkaline phosphatase activity did not bind to the resin. The flow through was next applied to a Q-Sepharose FF column (Pharmacia) equilibrated in 25 mM Tris-HCl pH 7.4 and 100 mM NaCl. The column was developed with a linear gradient from 100 to 350 mM NaCl in 25 mM Tris-HCl pH 7.4. Alkaline phosphatase eluted at~250 mM NaCl. Appropriate fractions were pooled, supplemented to 1 mM $MgCl_2$ and resolved on hydroxylapatite (BIO-RAD) equilibrated in 25 mM Tris-HCl pH 7.4 and 10 mM NaCl (Buffer A). The enzyme activity was eluted with a linear gradient from 100% Buffer A to 100% Buffer B (50 mM Na phosphate pH 7.0). Fractions containing alkaline phosphatase activity were pooled, equilibrated into 50 mM Tris-HCl pH 9.3 and 25 mM NaCl (Buffer A) on Centriprep-30 concentrators (Amicon) and applied to a Q-Sepharose FF column equilibrated in Buffer A. The enzymatic activity was eluted with a linear gradient from 25 to 600 mM NaCl in Buffer A. Pooled fractions were exchanged into 25 mM Tris-HCl pH 7.4 and 25 mM NaCl as described above and applied to a DEAE-Sephacel column (Pharmacia) in the same buffer. Alkaline phosphatase was eluted with a linear gradient from 25 to 300 mM NaCl in 25 mM Tris-HCl. Appropriate DEAE-Sephacel fractions were combined, exchanged into 25 mM Tris-HCL pH 7.4, 25 mM NaCl and 50 mM $MgCl_2$ on a Centriprep 30 apparatus and heated at 100° C. for 10 minutes. Insoluble, heat-denatured proteins were removed by centrifugation.

Characterization:

Following the above purification procedure analysis of the preparation by SDS-PAGE revealed that enzyme subunits corresponded to two closely spaced polypeptides which migrated at an apparent molecular weight of approximately 55,000 daltons (FIG. 1). The gel used was purchased from BioRad as a Mini-Protein II Ready Gel, Catalogue No. 161-0902, 4–15% gradient gel and used according to the manufacturer's specifications. The presence of two protein bands, both of which display enzyme activity, may represent isozymes of the same protein, a post-translationally modified form of the enzyme, a partial proteolytic cleavage or possibly an artifact of the purification procedure. If the latter is true, then those skilled in the art recognize that the enzyme may be purified by other procedures which may or may not yield two polypeptides.

Figure 2:
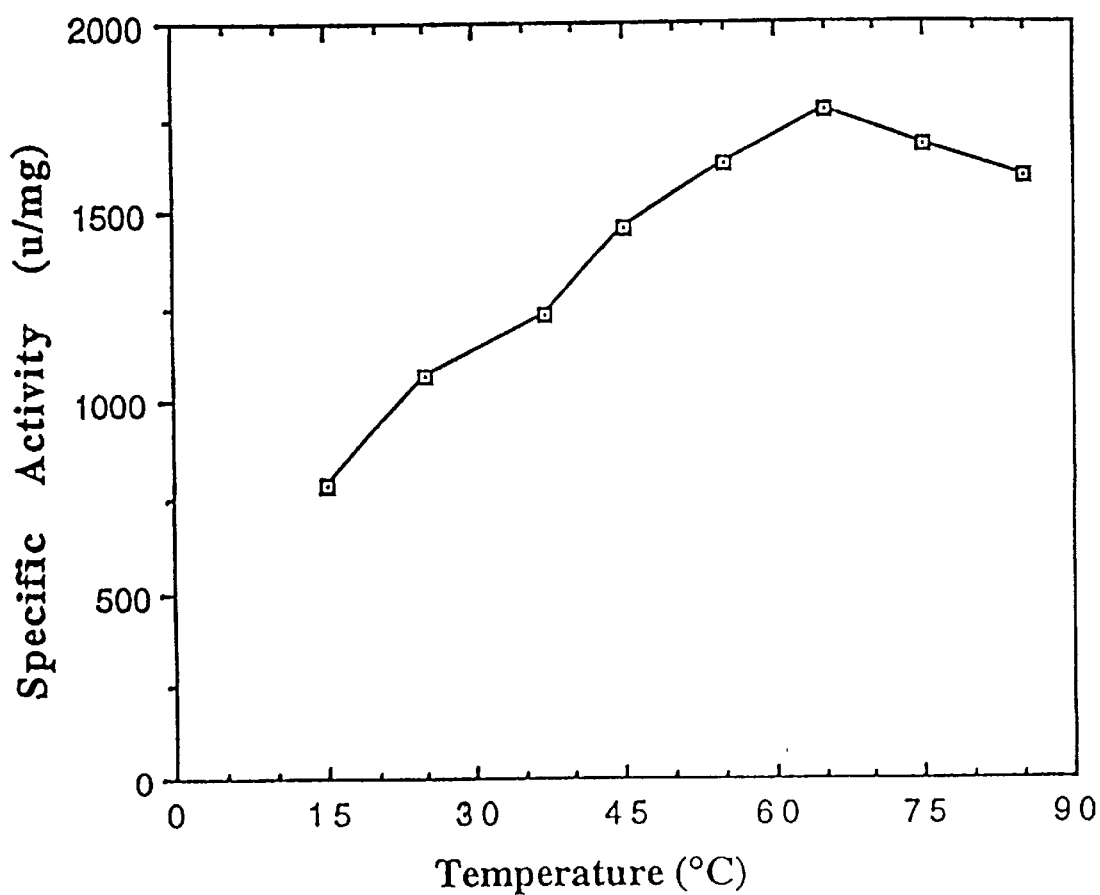
Figure 3:
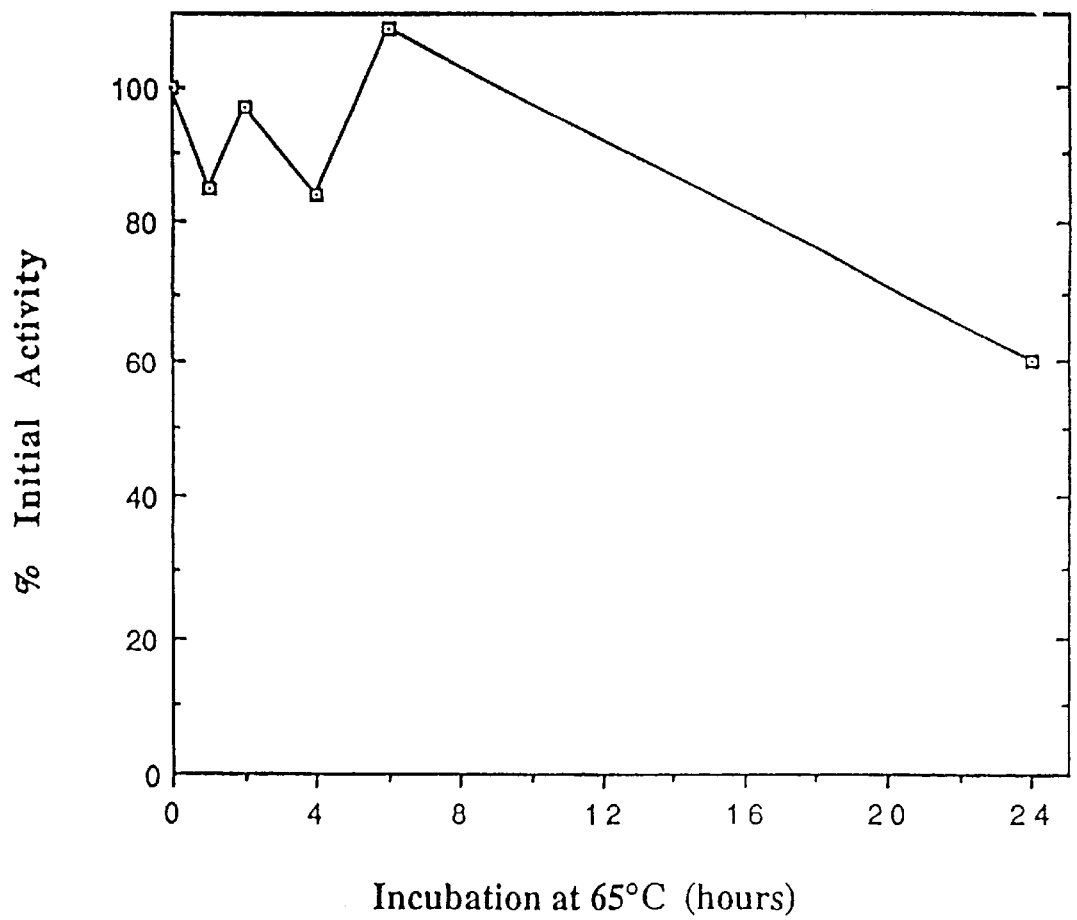
Figure 4:
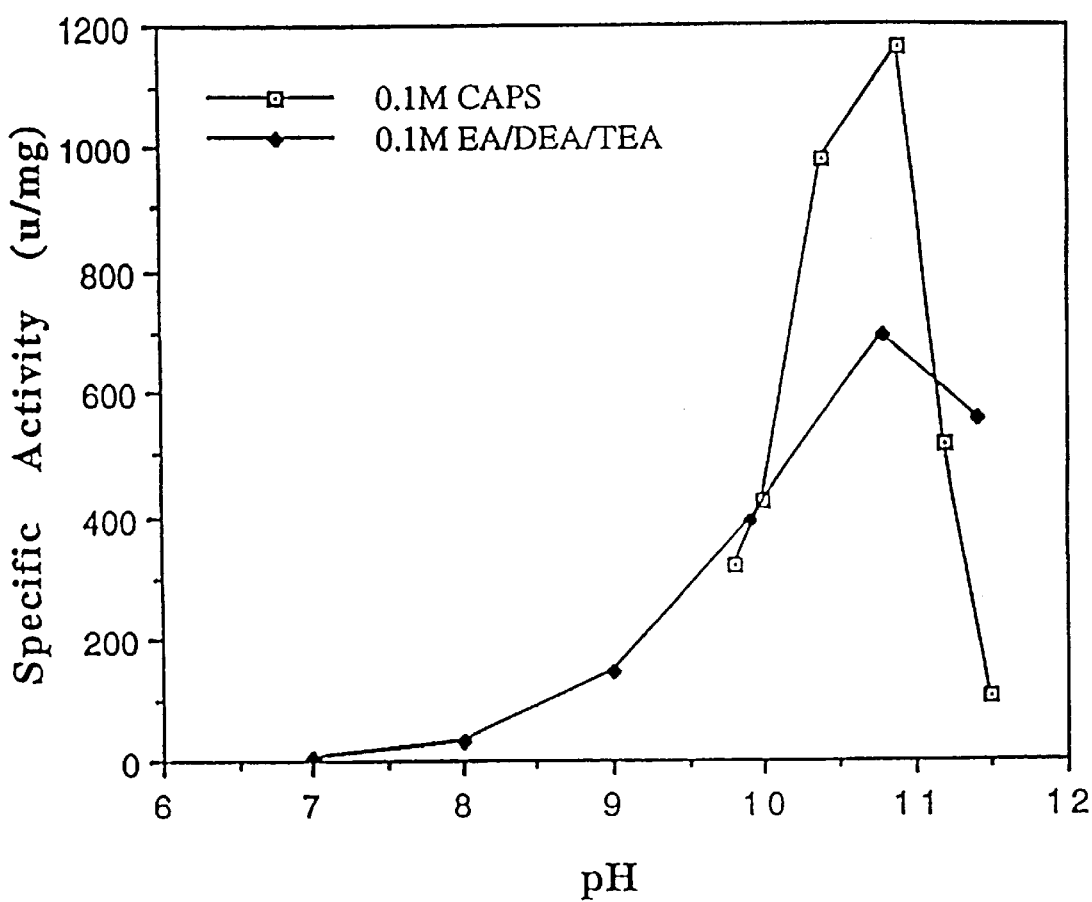

The final product represented a greater than 350-fold purification of the crude cell lysate as determined by specific activity studies. The enzyme preparation was further characterized by determining the temperature and pH of optimal enzyme activity. To determine the temperature of optimal enzyme activity, stock alkaline phosphatase (0.32 mg/ml) was diluted 250-fold in 25 mM Tris-HCl pH 7.4, 25 mM NaCl and 1 mM $MgCl_2$ and assayed for activity under standard conditions (see above) at the indicated temperatures. Results are presented in FIG. 2. To determine the pH of optimal enzyme activity, stock alkaline phosphatase was diluted 200-fold in 25 mM Tris-HCl pH 7.4, 25 mM NaCl and 1 mM MgCl. Enzyme assays were performed (as above) at the indicated pH values at 37° C. in either 0.1M CAPS, 1 mM $MgCl_2$ and 6 mM pNPP or 0.1M each of ethanolamine, diethanolamine, triethanolamine, 1 mM $MgCl_2$ and 6 mM pNPP. Results are presented in FIG. 4. To determine enzyme stability at 65° C., stock alkaline phosphatase was diluted 20-fold in 25 mM Tris-HCl pH 7.4, 25 mM NaCl, 1 mM $MgCl_2$ and 15% glycerol and incubated at 65° C. for the indicated times. Samples were diluted an additional 10-fold prior to activity assays performed under standard conditions. Results are presented in FIG. 3.

Figure 5:
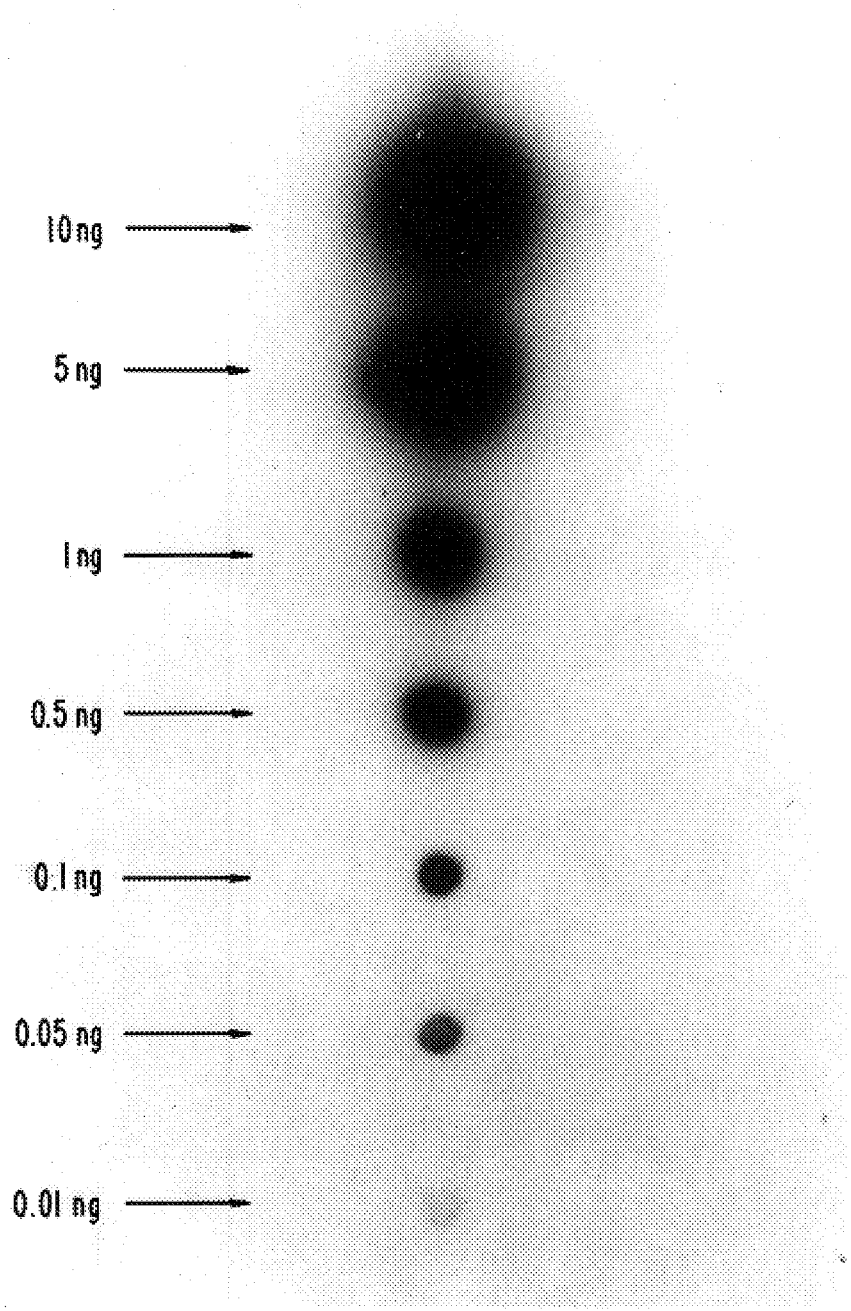

The alkaline phosphatase was also used in the non-isotopic detection of dot-blotted DNA (FIG. 5). Target DNA (λ-Hind III) was denatured in TE+0.2M NaOH and spotted in the various amounts (0.01 ng, 0.05 ng, 0.1 ng, 0.5 ng, 1 ng, 5 ng, 10 ng) onto a nylon membrane (Biodyne A; Pall) and fixed by baking for 1 hour at 80° C. The membrane was prehybridized for 1.5 to 2 hours at 65° C. in ECL Gold hybridization buffer (Amersham) supplemented with 400 mM NaCl, 4% casein and 50 mM $MgCl_2$. Probe was prepared by crosslinking R. marinus alkaline phosphatase to λ-Hind III DNA. Equal volumes (typically 10 ul each) of heat denatured probe (10 ng/ul in 10 mM Na phosphate pH 5.5), alkaline phosphatase (60 ng/ml in 10 mM Na phosphate pH 5.5) and glutaraldehyde (1.5%) were mixed and incubated at 37° for 45 minutes. The enzyme/probe complex was added directly to the prehybridization reaction (10 ng probe/ml hybridization buffer) and allowed to hybridize overnight at 65° C. Following hybridization, the membrane was washed as follows: 2× SSC, 25 mM Tris pH 7.4, 10 mM $MgCl_2$, 0.1% SDS (3×5 minutes at room temperature); 0.2× SSC, 25 mM Tris pH 7.4, 10 mM $MgCl_2$ (3×5 minutes at 37° C.); 0.1M CAPS pH 10, 15% glycerol, 2 mM $MgCl_2$ (30 minutes at room temperature). After washing the membrane was placed in a seal-a-meal bag with ~20 ul CDP-Star substrate (Tropix) per $cm^2$ membrane and exposed to autoradiography film for 1 minute.

EXAMPLE 2

Cloning of Rhodothermus marinus Alkaline Phosphatase

Genomic DNA was isolated from Rhodothermus marinus using standard procedures. Chromosomal DNA was subjected to partial Sau 3AI digestion and resolved by gel electrophoresis in low-melt agarose. Fragments ranging from 4–9 kb were isolated from the gel and ligated into pBluescript SK+ (Stratagene) which had been digested with BamHI and dephosphorylated. Following ligation, DNA was transformed into ultracompetent E. coli strain XL2-Blue MRF' (Stratagene) and plated on LB agar plates containing 100 ug/ml ampicillin, 50 ug/ml BCIP (5-bromo-4-chloro-3-indolyl phosphate, a chromogenic indicator) and 5 mM IPTG (isopropyl-β-D-thiogalactopyranoside). The plates were incubated overnight at 37° C. A single blue colony (pBRM1) was observed out of approximately 6000 transformants.

Clone pBRM1

Restriction analysis of clone pBRM1 indicated an insert of approximately 6 kb which encoded the alkaline phosphatase activity in cell lysates. No significant enzyme activity was observed in parallel studies performed with empty pBluescript vector. The alkaline phosphatase activity was found to be thermostable, as greater than 75% of enzyme activity was retained after heating for 10 minutes at 100° C. In-gel colorimetric assays performed on cell lysates which had been renatured following SDS-PAGE indicated that the enzymatic activity was localized to a polypeptide which migrated at an apparent molecular weight of ~46,000 Daltons. pBRM1 was transformed into E. coli CC118 [ara D139 Δ(ara, leu) 7697 Δlac X74 phoA Δ20 galE galK thi rpsE rpoB arg Eam recA1] and grown on BCIP indicator plates. This E. coli strain contains a deletion in the alkaline phosphatase (pho A) gene. The development of a blue colony indicated that the cloned enzyme is distinct from native E. coli alkaline phosphatase (BAP).

Clone pBRM1/KpnI

Mapping, deletion and expression studies indicated that approximately one half of the 6 kb insert in pBRM1 could be deleted without affecting enzyme activity. The smaller clone containing an insert of ~3 kb was designated as pBRM1/KpnI (SEQ ID NO. 1, See FIG. 7). To facilitate DNA sequencing, pBRM1/KpnI was digested with SacII to yield 0.45, 1.9 and 0.5 kb fragments which were individually subcloned into pBluescript.

Clone pCRM1.8

BLAST analysis (Gish et al., (1993) Nat. Genet. 3:266–72) of the DNA sequence data indicated that 1 kb of the insert did not code for alkaline phosphatase and thus could be deleted. pBRM1/KpnI was digested with HindIII/KpnI to release a 1.8 kb fragment which was subsequently subcloned into pUC19. The resultant clone was designated as pCRM1.8 (SEQ ID NO. 2, See FIGS. 8A & B).

Expression and Purification of Cloned Alkaline Phosphatase

An overnight culture of E. coli strain JM109 containing the recombinant plasmid pBRM1.8 was diluted 1:40 in LB.+100 ug/ml ampicillin and grown with shaking at 37° C. until the $A_{600}$ reached 1.30. The culture was induced by the addition of 2.5 mM IPTG and allowed to incubate for an additional 18 hours. The cells were pelleted by centrifugation at 6000×g for 20 minutes at 4° C. and stored at −80° C. Frozen cells (12 g) were thawed and resuspended in 60 ml of lysis buffer (25 mM Tris,HCL pH 7.4, 50 mM NaCl, 1 mM $MgCl_2$, 1 mM EDTA, 0.05% Triton X-100 and 1 mg/ml lysozyme). The resuspension was stirred occasionally for 45 minutes at 4° C., sonicated to reduce viscosity and clarified by centrifugation at 70,000×g for 30 minutes at 4° C. The supernatant was supplemented to a final concentration of 50 mM $MgCl_2$ and heated at 80° C. for 20 minutes to precipitate heat labile proteins which were subsequently removed by centrifugation as above. The supernatant was diluted 1:1 with Buffer A (25 mM Tris,HCL pH 7.4, 20 mM NaCl and 1 mM $MgCl_2$) to reduce salt concentration and chromatographed on DE 52 anionic exchange resin (Whatman). The column was developed with a 6-column volume linear gradient from 20 to 500 mM NaCl in Buffer A. Alkaline phosphatase activity eluted at ~180 mM NaCl. Appropriate fractions were pooled and applied to a hydroxylapatite column (Bio-gel HTP; BioRad) equilibrated in 25 mM Tris.HCL pH 7.4 and 20 mM NaCl (Buffer B). The column was washed with two column volumes of Buffer B to remove residual $MgCl_2$ and then developed with an 8-column volume linear gradient of Buffer A to 150 mM Na phosphate pH 7.0. Alkaline phosphatase eluted at a phosphate concentration of ~40 mM. Pooled fractions were diluted 1:1 in Buffer B and applied to a Q Sepharose FF anion exchange column (Pharmacia). The column was washed with Buffer B to remove residual phosphate and then developed with a 10-column volume linear gradient of 20 to 500 mM NaCl in Buffer A. Enzyme activity was found to elute at ~250 mM NaCl. The final product was found to be greater than 90% pure as determined by SDS-PAGE with a specific activity of ~3000 units/mg. The cloned protein has an apparent molecular weight which is less than that of native protein isolated from R. marinus. Protein sequencing of the amino terminus of both proteins revealed that the majority of the mature alkaline phosphatase isolated from R. marinus begins at serine residue 22 (SEQ ID NO. 4, See FIGS. 9A & B), whereas the protein isolated from E. coli begins at glutamine residue 21. The difference in apparent molecular weight between the two proteins therefore is not due to a truncation at the amino terminus of the cloned protein. Amino acids upstream of these residues are presumed to function as signal peptides, as alkaline phosphatase is a periplasmic enzyme in E. coli and other bacteria.

DNA Probe Labelled with Cloned Rhodothermus marinus alkaline phosphatase

Figure 6:
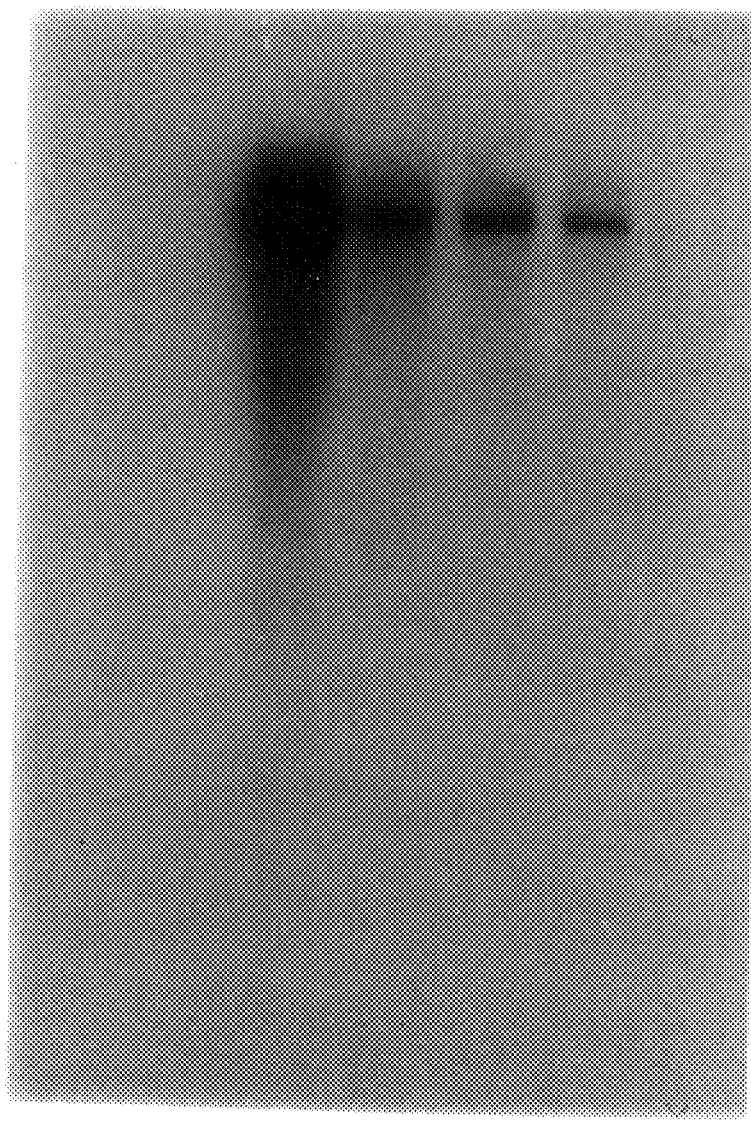

Cloned alkaline phosphatase was used for the non-isotopic detection of human genomic DNA (FIG. 6) The N-ras gene is easily detected in a 0.1 μg sample of total human genomic DNA by Southern blot analysis. The blot was prepared by fractionating a Hind III digestion of genomic DNA through a 1.0% agarose gel followed by capillary transfer onto a Hybond N membrane (Amersham) using 10× SSC buffer. The membrane was prehybridized for 1.5 to 2 hours in modified ECL Gold hybridization buffer (from Amersham, 2M urea in place of 6M urea, 0.2% SDS in place of 0.4% SDS) supplemented with 400 mM NaCl, 4% casein and 20 mM $MgCl_2$. The probe was prepared by cross-linking cloned R. marinus alkaline phosphatase to N-ras DNA. Equal volumes (typically 10 μl each) of heat denatured probe (10 ng/ml in water), cloned alkaline phosphatase diluted immediately prior to use (40 ng/ml in 10 mM MES buffer pH 5.0) and formaldehyde (2% in water) were mixed and incubated at 37° C. for 30 minutes. The probe was added directly to the prehybridization reaction (5 ng/ml hybridization buffer) and allowed to hybridize overnight at 50° C. Following hybridization, the membrane was washed as follows: one rinse and then 2×10 minute washes with the following buffer preheated to 50° C. (washing was done on a shaker platform at RT): 100 mM Na phosphate pH 7.0, 150 mM NaCl, 2M urea, 0.4% SDS, 10 mM $MgCl_2$. This was followed by one rinse and then 2×5 minute washes with the following buffer preheated to 55° C. (wash at RT): 100 mM Na phosphate pH 7.0, 150 mM NaCl, 10 mM $MgCl_2$. The last rinse was done at RT with 50 mM Tris pH 10, 100 mM NaCl, 2 mM Mg $Cl_2$. The membrane was placed in a sealed plastic bag with 20 μl CDP-star substrate (Tropix) per $cm^2$ membrane and exposed to autoradiography film for 2 hours.

Thermus thermophilus

EXAMPLE 3

Alkaline Phosphatase from Thermus thermophilus

Thermus thermophilus strain HB8 was grown under aerobic conditions at 75° C. in a defined media (modified from Yeh and Trela; 251 J. Biol. Chem. 3134, 1976) containing limiting amounts of inorganic phosphate which causes a derepression of alkaline phosphatase in this organism. The culture media contained the following salts per liter: 100 mg nitrilotriacetic acid, 60 mg $CaSO_4.2H_2O$, 100 mg $MgSO_4.7H_2O$, 8 mg NaCl, 105 mg $KNO_3$, 5 mg $ZnSO_4.7H_2O$, 5 mg $H_3BO_3$, 0.16 mg $CuSO_4.5H_2O$, 0.25 mg $Na_2MoO_4.2H_2O$, 0.4 mg $CoCl_2.6H_2O$, 22 mg $MnSO_4.H_2O$, 0.28 mg $FeCl_3.6H_2O$. Vitamins were added as follows per liter: 0.1 mg biotin, 0.1 mg thiamin and 0.05 mg niacin. The media was further supplemented to 0.3% L-glutamic acid, 0.004% L-lysine, 0.1% glycerol and 0.1% glucose. Sodium glycerophosphate (40 μM) served as the source of phosphate. The pH of the media was adjusted to 7.2. Cells were harvested by continual flow centrifugation and stored frozen at −80° C.

Alkaline phosphatase activity was measured spectrophotometrically at 405 nm by following the increase in absorbance due to the release of p-nitrophenol from p-nitrophenyl phosphate (pNPP) by the enzyme at 37° C. The assay buffer contained 6 mM p-nitrophenyl phosphate, 100 mM CAPS (pH 11), and 15% glycerol unless noted otherwise.

Frozen cells were thawed, resuspended in 10 mM Tris-HCl (pH 8), 1M $MgCl_2$ and 1 mM $CaCl_2$ and lysed by sonication. The lysate was cleared of cellular debris by centrifugation, dialyzed against 20 mM Tris, pH 8.0, 25 mM $MgCl_2$, 1 mM $CaCl_2$ and 0.1% Triton X 10) (buffer A) before applying to a DE52 anionic exchange column equilibrated in buffer A. The majority of alkaline phosphatase activity appeared in the flow through which was adjusted to pH 6.0 by the addition of 25 mM MES (free acid) and subsequently applied to a Heparin Sepharose CL-6B cationic exchange column. The column was developed with a linear gradient from 0 to 800 mM NaCl ($MgCl_2$ and Triton were omitted from the high salt buffer).

Fractions containing alkaline phosphatase activity (~300 mM NaCl) were pooled and applied directly to a hydroxylapatite column which was washed extensively with 20 mM Tris pH 7.4 and then developed with a linear gradient from 20 to 500 mM Na Phosphate pH 7.0. The majority of alkaline phosphatase activity eluted at ~100 mM Na Phosphate.

Fractions containing enzyme activity were pooled and applied to P-11 phosphocellulose (Whatman) equilibrated in 100 mM Na phosphate pH 7.0. The majority of alkaline phosphatase activity was found in the flow through which was subsequently dialyzed against 30 mM Tris.HCl pH 8.8. The dialyzed material was applied to a Q-Sepharose anionic exchange column and developed with a linear gradient from 0 to 400 mM NaCl in 30 mM Tris.HCl pH 8.8. Alkaline phosphatase activity eluted at approximately 200 mM NaCl.

Analysis of the preparation by SDS-PAGE indicated that the peak of enzyme activity corresponded to a protein band which migrated at an apparent molecular weight of ~50,000 daltons. The final product was greater than 90% pure for the 50 kD polypeptide and represented a greater than 100-fold purification from the crude extract as determined by specific activity.

Figure 10:
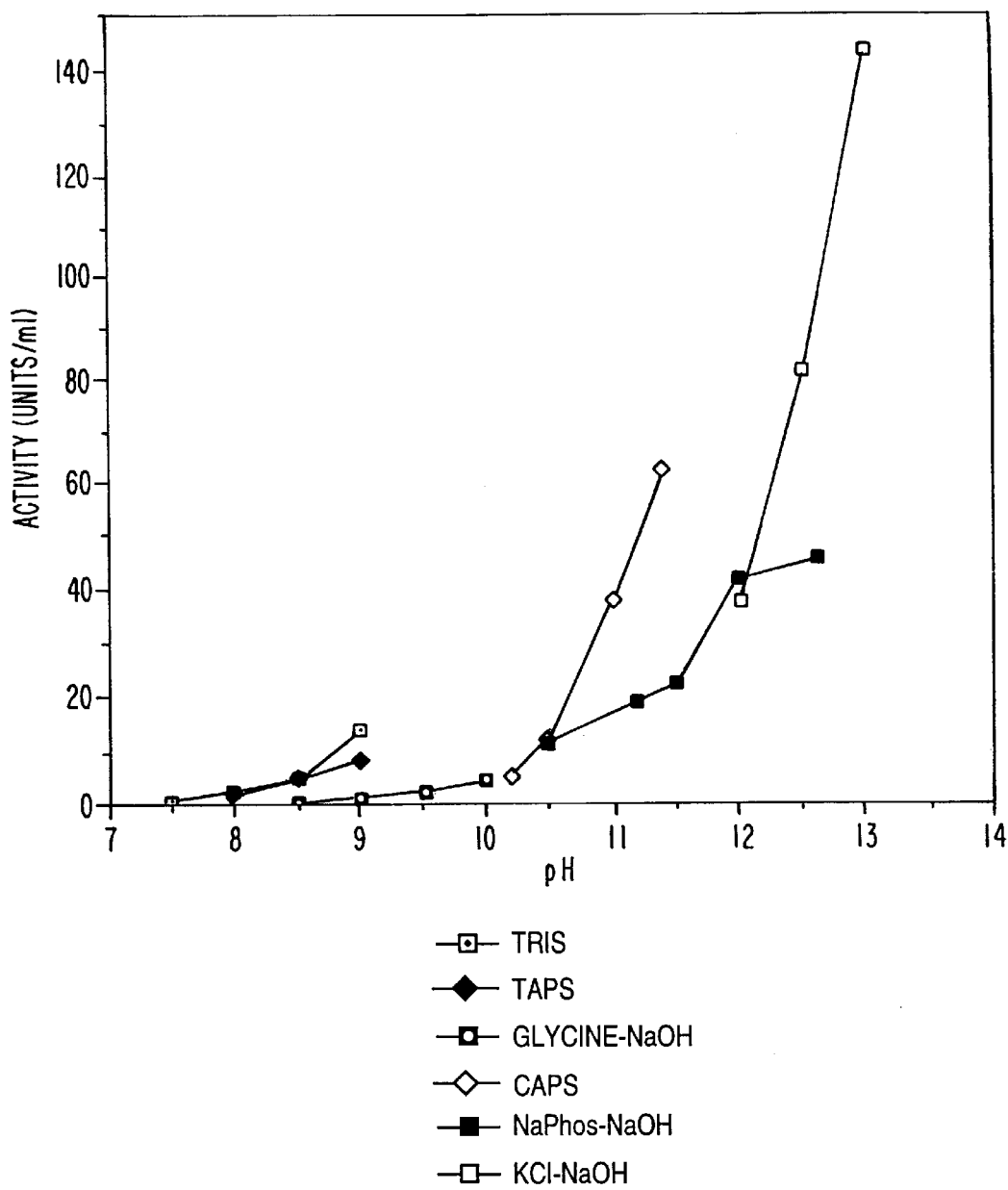
FIG. 10 is a graphical representation showing the pH activity of a thermostable alkaline phosphatase from *Thermus thermophilus*.
Figure 11:
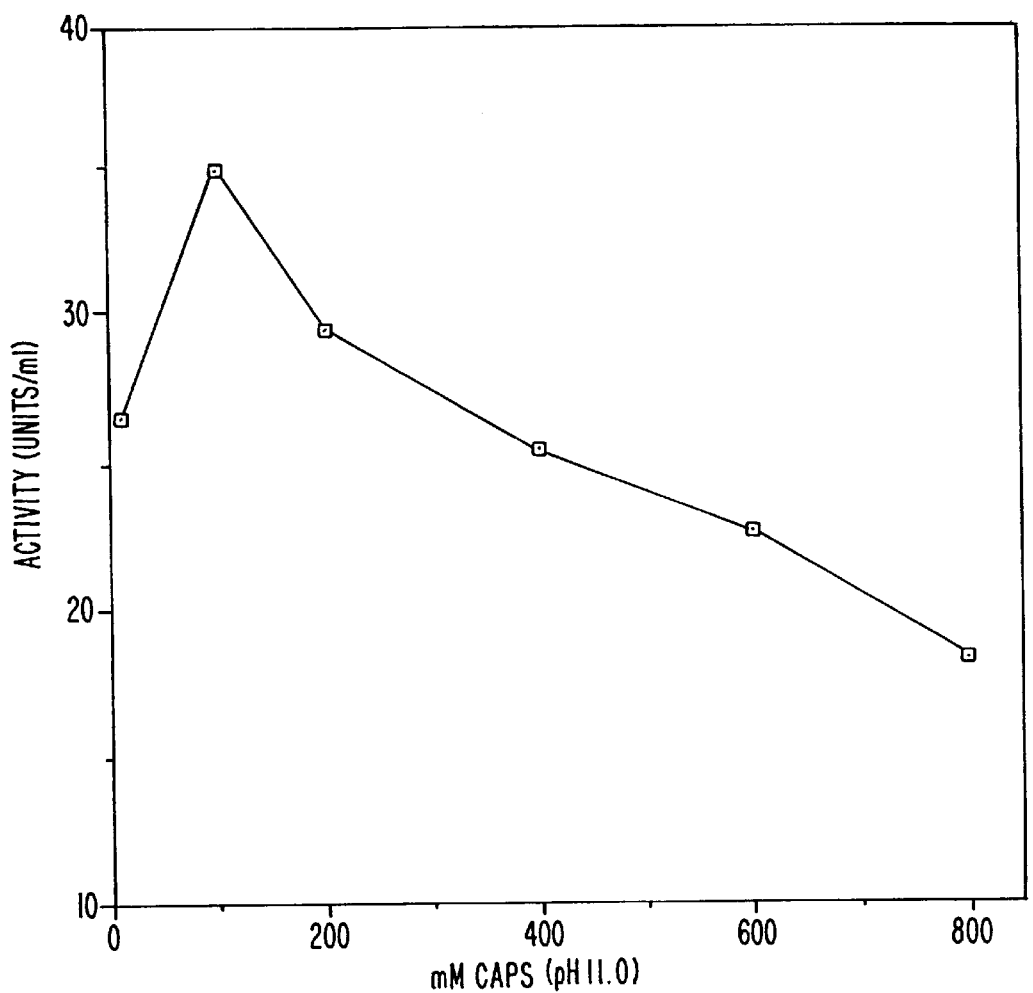
FIG. 11 is a graphical representation showing the activity (optimum) of a thermostable alkaline phosphatase from *Thermus thermophilus* of the present invention in various concentrations of CAPS buffer at pH 11.0.
Figure 12:
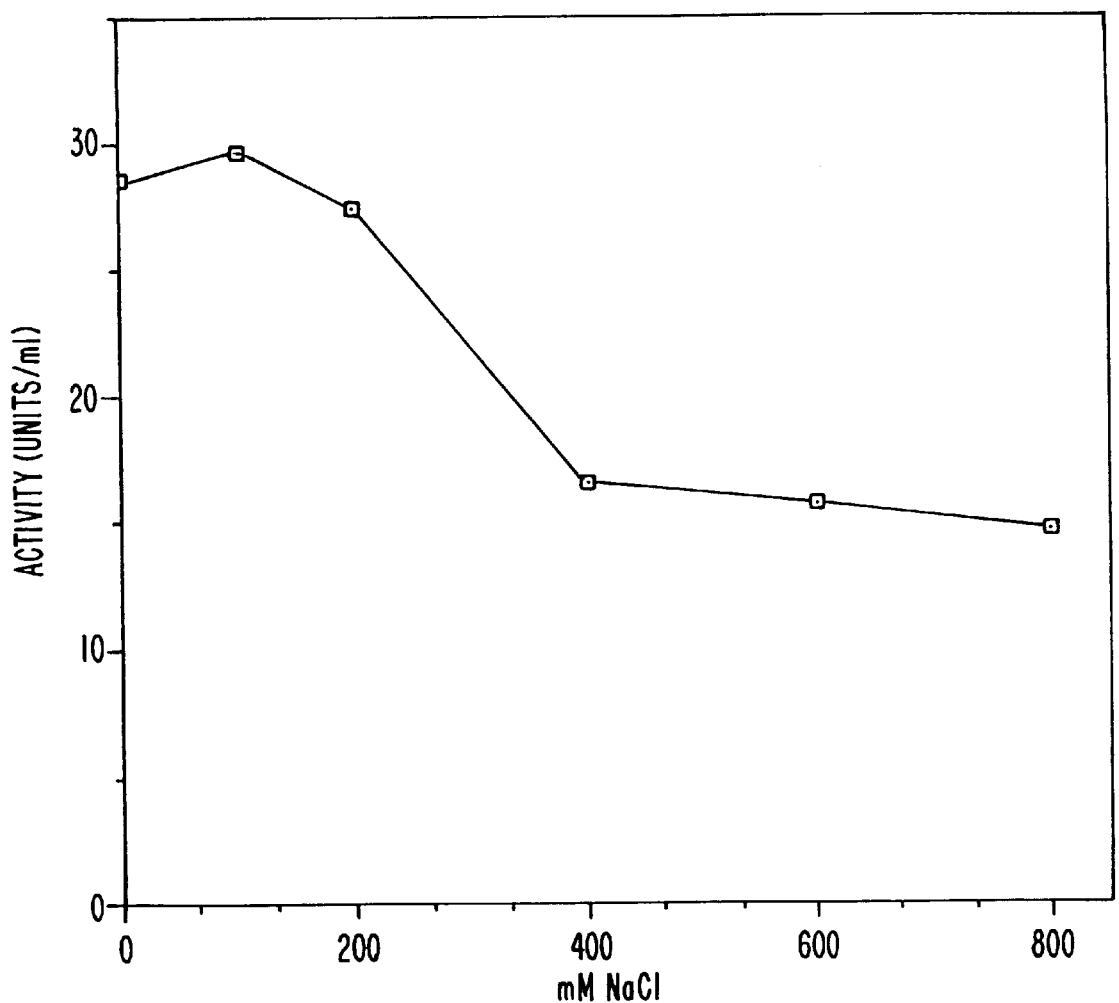
FIG. 12 is a graphical representation showing the activity (optimum) of a thermostable alkaline phosphatase from *Thermus thermophilus* of the present invention in various concentrations of NaCl.
Figure 13:
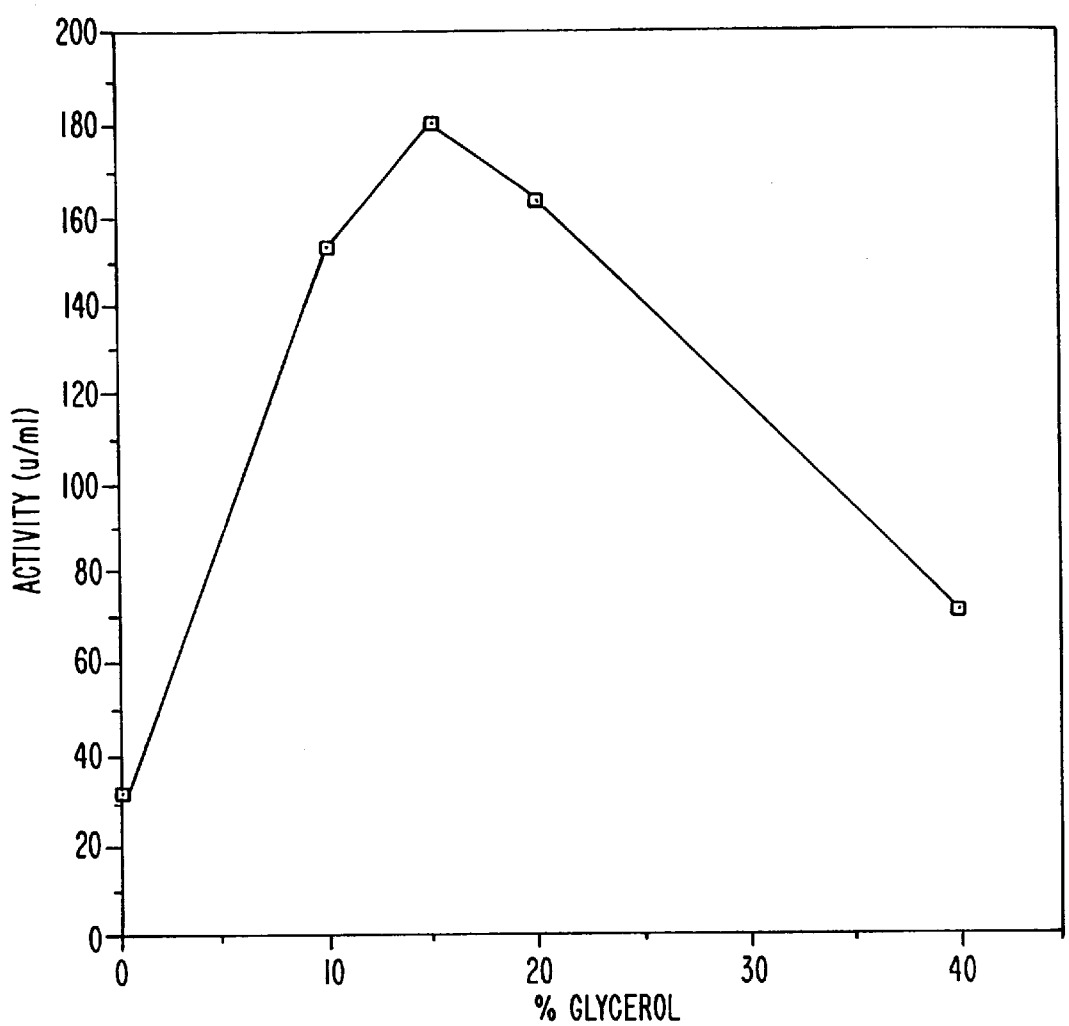
FIG. 13 is a graphical representation showing the activity (optimum) of a thermostable alkaline phosphatase from *Thermus thermophilus* enzyme of the present invention in various concentrations of glycerol.
Figure 14:
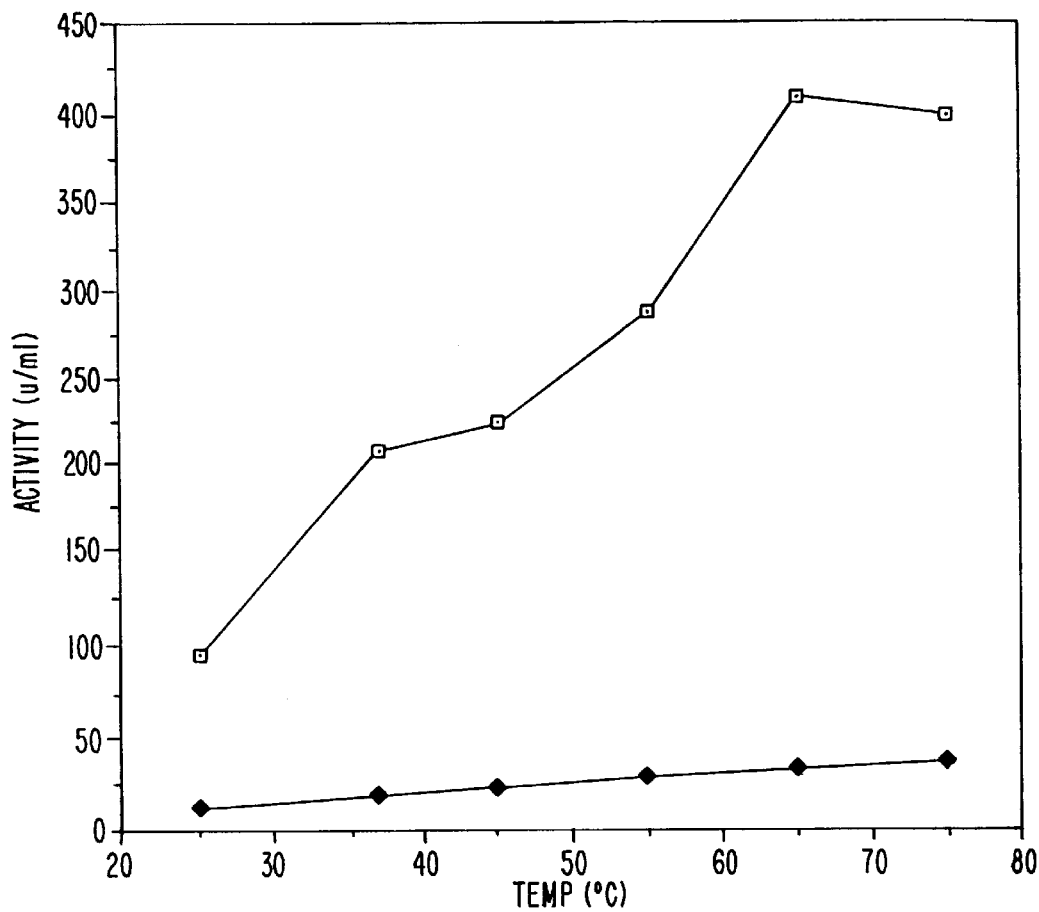
FIG. 14 is a graph showing the activity (optimum) of of a thermostable alkaline phosphatase from *Thermus thermophilus* of the present invention at various temperatures.
Figure 15:
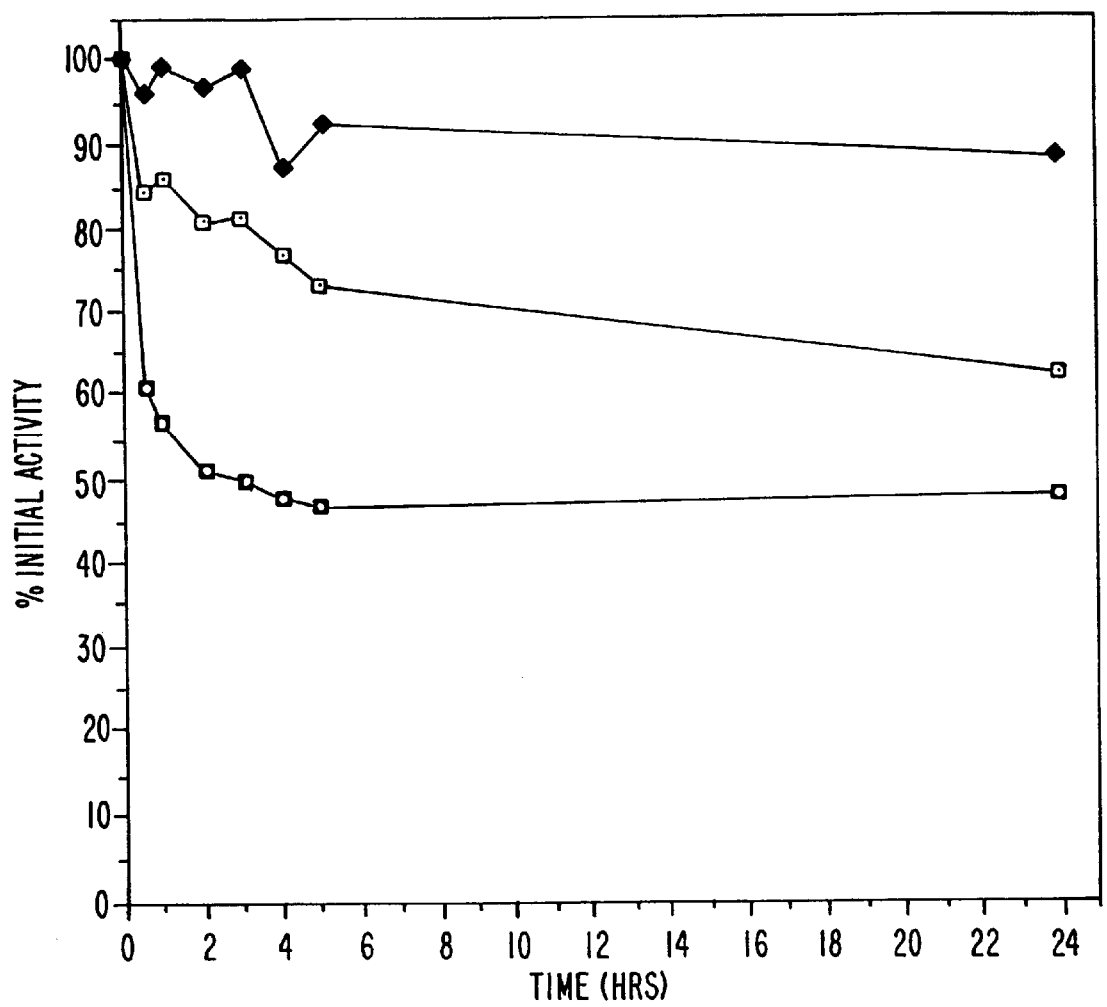
FIG. 15 is a graph showing the stability of a thermostable alkaline phosphatase from *Thermus thermophilus* after heating at 70° C. for up to twenty four hours in various buffers.

Tth alkaline phosphatase displays measurable activity over a rather broad range of pH values, but appears to have an unusually high pH optimum, with 13.0 being the highest assayed (FIG. 10). Since applications at such an extreme pH are infrequent, most of the characterizations were carried out at pH 11.0. Under optimized conditions (100 mM CAPS pH 11.0, 15% glycerol) the enzyme displays a specific activity of $\geq$250 units per mg at 37° C. Enzyme activity is affected by a variety of other factors, including buffer (FIGS. 10 and 14), ionic strength (FIGS. 11 and 12), glycerol (FIG. 13) and temperature (FIG. 14). The enzyme also appears to have a requirement for divalent cation as it is inhibited by 1 mM EDTA (data not shown). However, the addition of $Ca^{++}$, $Mg^{++}$, $Mn^{++}$, $Co^{++}$, $Cu^{++}$, or $Zn^{++}$ to the assay mixture either failed to stimulate activity or was found to be inhibitory. More routine experiments can readily determine metal ion requirements of this enzyme. The protein appears to be quite thermostable as it retains nearly 90% of its activity after 24 hours incubation at 70° C. (FIG. 15). While more active in CAPS buffer, the enzyme appears to be more stable in Tris. It is unclear whether the activity in Tris is due to a pH effect or a buffer effect, but the enzyme activity is stimulated by high concentrations of this buffer In addition, the broad temperature activity range of this enzyme (FIG. 14), permits flexibility in choice of assay temperature. Finally, the extremely high pH optimum of Tth alkaline phosphatase may make it uniquely suitable for applications at high pH.

When using streptavidin conjugated alkaline phosphatase on positively charged membranes, as in nucleic acid hybridization, pH greater than 9.5 is preferred to give decreased background.

If an enzyme is desired which is stable at 65°–75° C., it is possible to enhance the chances of discovery of such an enzyme by trying to isolate novel organisms that grow well at those temperatures. One could also select for organisms that are tolerant of high pH. In addition, knowing that an alkaline phosphatase is desired, one can then screen organisms, or libraries of recombinant clones, for alkaline phosphatase activity by use of the compound 5-bromo-4-chloro-3-indolyl phosphate (X-Phos). A blue color is obtained when the phosphate group is removed from this compound, making it very convenient to screen for activity. A pH activity profile would then be prepared to determine whether the phosphate removing activity was an alkaline phosphatase.

*Thermosipho africanus*

EXAMPLE 4

Alkaline Phosphatase from *Thermosipho africanus*

*Thermosipho africanus*, strain DSM 5309 was grown under anaerobic conditions at 75° C. as described by Huber et al., 12 *System. Appl. Microbiol.* 38, pp. 32–37, 1989. Cells were harvested by continual flow centrifugation and stored at −80° C.

Alkaline phosphatase activity was measured spectrophotometrically at 405 nm by following the increase in absorbance due to the release of p-nitrophenol from p-nitrophenyl phosphate by the enzyme at 37° C. The assay buffer contained 6 mM p-nitrophenyl phosphate, 100 mM Glycine-NaOH (pH 10), 1 mM $MgCl_2$ and 1 mM $ZnCl_2$.

Frozen cells were thawed, resuspended in 20 mM Tris-HCl (pH 8), 50 mM NaCl, 10% glycerol, 1 mM EDTA, 1 mM DTT (Buffer A) and lysed by sonication. The lysate was cleared of cellular debris by centrifugation before applying to a DE52 anionic exchange column (typically 10 grams resin per gram of cells). The column was developed with 10 column volumes of a linear gradient from 50 to 1000 mM NaCl in Buffer A. The majority of alkaline phosphatase activity eluted at a salt concentration of about 400 mM. Appropriate fractions were pooled, dialyzed extensively against 25 mM HEPES-KOH (pH 7.25), 10 mM KCl, 10% glycerol, 1 mM EDTA, 1 mM DTT and applied to a Heparin Sepharose CL-6B column. Enzyme activity was found in the flow-through, which was subsequently applied to a P11 phosphocellulose column. The P11 flow-through was chromatographed on Affi-Gel Blue affinity resin. The enzyme did not bind to this column and therefore the flow-through was extensively dialyzed against Buffer A and applied to a Q-Sepharose anionic exchange column which was developed with a linear gradient from 50 to 800 mM NaCl. While the elution profile exhibited several minor peaks of activity, the majority of alkaline phosphatase activity appeared in the flow-through.

In light of the fact that this enzyme did not bind to most of the resins tested, the Q-Sepharose flowthrough was rechromatographed on DE52 resin as described above except using a slightly shallower gradient from 50 to 800 mM NaCl. The major activity peak eluted at about 360 mM salt. The peak fractions were pooled, dialyzed extensively against 20 mM $KPO_4$, 50 mM KCl, 10% glycerol, 1 mM DTT and chromatographed on hydroxylapatite. The column was developed with a linear gradient from 20 to 600 mM $KPO_4$. The peak alkaline phosphatase activity eluted at about 100 mM $KPO_4$. After pooling, the peak fraction was supplemented to a final concentration of 0.1 mM EDTA, 1 mM $MgCl_2$, 1 mM $ZnCl_2$ and stored at 40°C.

Figure 17:
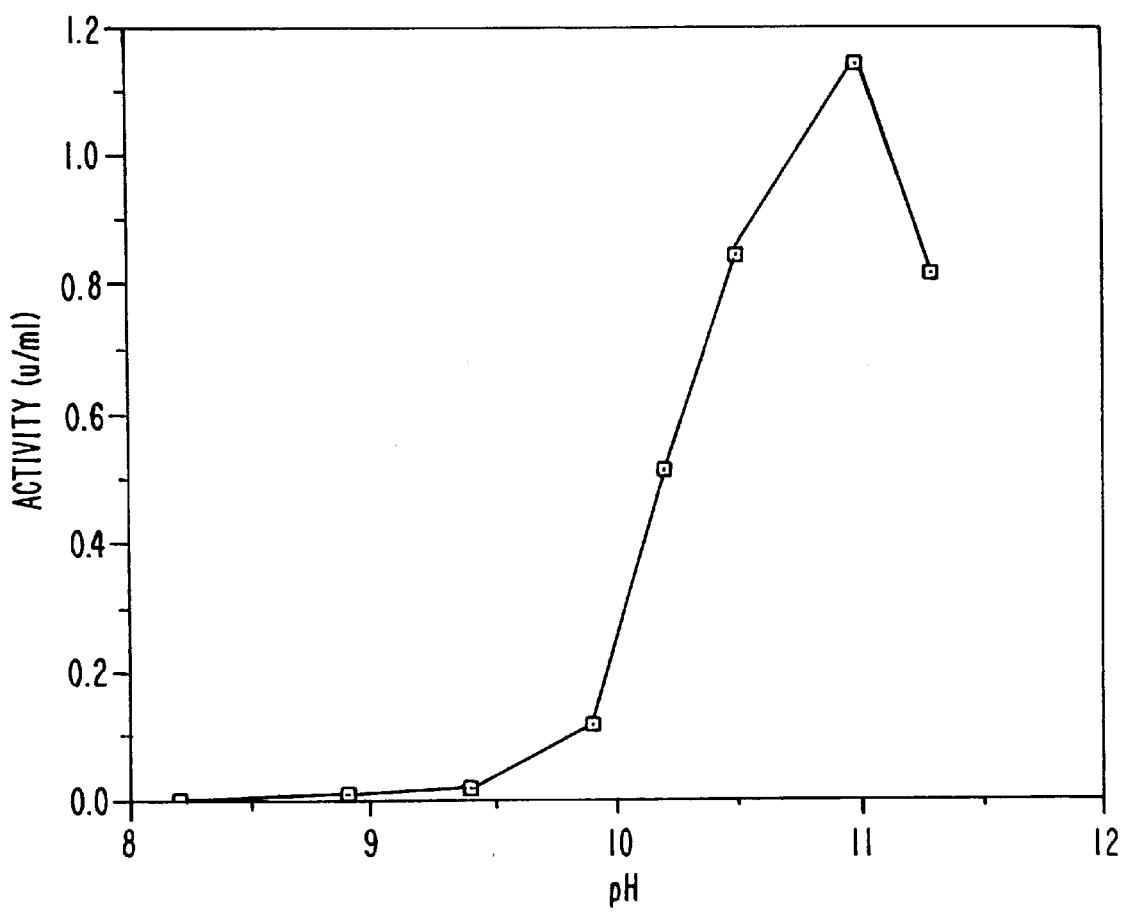
FIG. 17 is a graphical representation showing the pH optimum of a thermostable alkaline phosphatase from *Thermosipho africanus* of the present invention.
Figure 18:
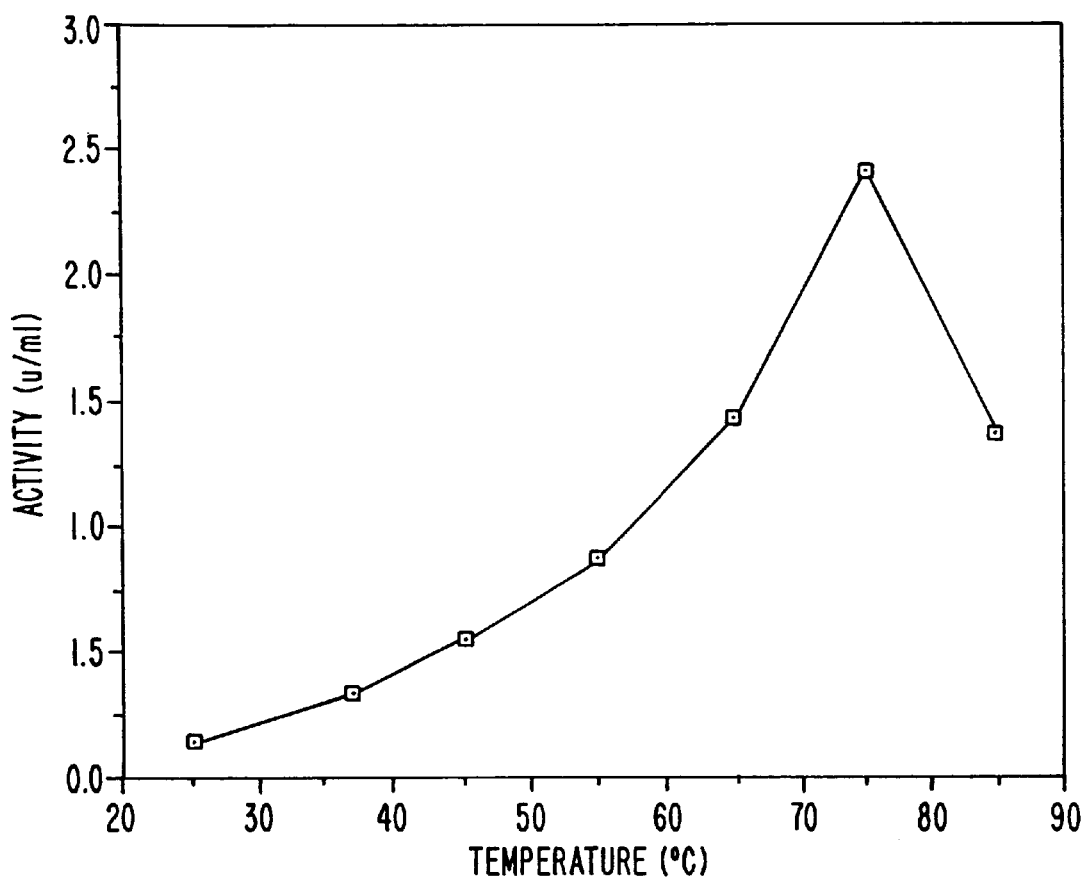
FIG. 18 is a similar graph showing the temperature optimum of a thermostable alkaline phosphatase from *Thermosipho africanus*.
Figure 19:
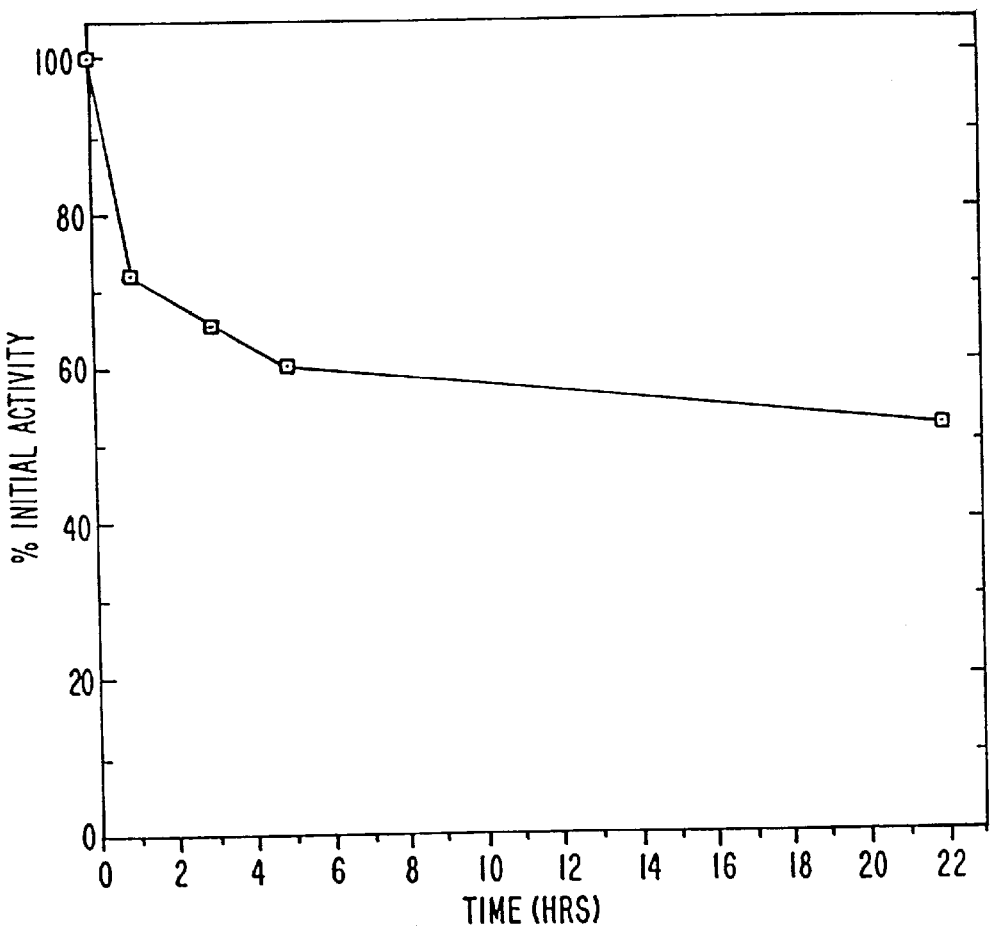
FIG. 19 is a graph showing the stability of a thermostable alkaline phosphatase from *Thermosipho africanus* after heating at 65° C. for up to twenty-two hours.

Analysis of this preparation by SDS-PAGE revealed several major protein bands, therefore the apparent molecular weight of the alkaline phosphatase was not determined. While not purified to homogeneity, the final product did represent a 69-fold purification of the crude extract as determined by specific activity studies. The enzyme preparation was further characterized by determining the pH optimum (FIG. 17), the temperature optimum (FIG. 18) and enzyme stability at 65° C. (FIG. 19), using standard methods.

EXAMPLE 5
Purification and Characterization of a thermostable Alkaline Phosphatase from *Thermosipho africanus*

*Thermosipho africanus*, strain DSM 5309 was grown in a modified form of DSM media 141, under anaerobic conditions at 75° C. as described by Huber et al., (System. Appl. Microbiol. 12:38–47 (1989)). Cells were harvested and stored at −80° C. as above.

Alkaline phosphatase activity was measured spectrophotometrically at 405 nm by following the increase in absorbance due to the release of p-nitrophenol from p-nitrophenyl phosphate (pNPP) by the enzyme at 37° C. The assay buffer was as above, or contained 100 mM CAPs (pH 11), 1 mM $MgCl_2$ and 6 mM pNPP.

Alkaline phosphatase was released from bacterial cells by osmotic shock. 30 grams of frozen cells were resuspended in 75 ml of 25 mM Tris pH 7.4, 25 mM NaCl and 2 mM EDTA (Buffer C) and mixed on a magnetic stir plate for one hour at room temperature. The lysate was cleared of cellular debris by centrifugation before applying to a DE 52 anionic exchange column (Whatman; 0.5 grams resin per gram frozen cells) equilibrated in Buffer C. The majority of alkaline phosphatase activity appeared in the flow-through which was supplemented to 1 mM $MgCl_2$ and subsequently applied to a Heparin Sepharose CL-6B column (Pharmacia) which was developed with 12.5 column volumes of a linear gradient from 25 to 1000 mM NaCl in Buffer C plus 1 mM $MgCl_2$. Enzyme activity eluted at about 450 mM NaCl. Peak fractions were pooled and applied to a hydroxylapatite column (Bio-Rad) which was washed with two column volumes of 25 mM Tris pH 7.4 followed by 13 column volumes of a linear gradient from 10 to 300 mM Naphosphate pH 7.0. Enzyme activity eluted at about 150 mM Na phosphate. Appropriate fractions were pooled, buffer exchanged into 25 mM Tris pH 9.0 on a Centriprep 30 apparatus (Amicon) and chromatographed on Q-Sepharose FF anionic exchange resin (Pharmacia). The column was developed with 12 volumes of a linear gradient from 0 to 300 mM NaCl in 25 mM Tris pH 9.0. The majority of alkaline phosphatase activity eluted at about 80 mM NaCl.

Figure 20:
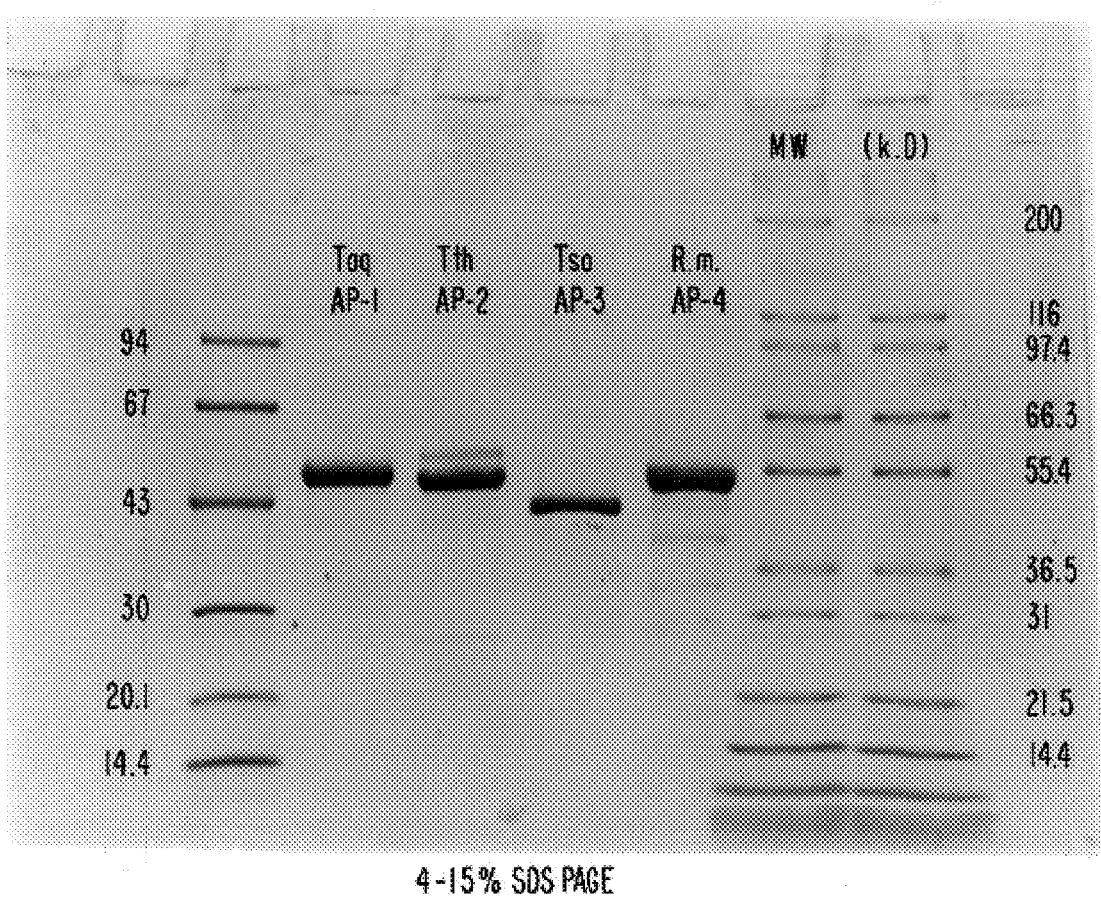
FIG. 20 is a copy of a 4–15% SDS PAGE comparing molecular weights of various alkaline phosphatases.

Analysis of this preparation by SDS-PAGE revealed a single protein band which migrated at an apparent molecular weight of approximately 47,000 daltons (FIG. 20). The final product represented a greater than 1000-fold purification of the crude extract as determined by specific activity studies. The enzyme preparation was further characterized by determining the pH optimum, the temperature optimum and enzyme stability at 65° C. (as above) and partial amino acid sequence (SEQ ID NO. 5) (See FIG. 21).

EXAMPLE 6
Comparison of Thermostable Alkaline Phosphatases Isolated from Thermophilic Bacteria Alkaline phosphatase isolated from three thermophilic bacteria was used for the non-isotopic detection of dot-blotted DNA (FIG. 22). Target DNA (lambda DNA/HindIII digestion) was denatured in TE plus 0.2M NaOH by heating at 37° C. for five minutes, and then neutralized with 0.2M HCl. Samples were spotted in various amounts (100 pg, 50 pg, 10 pg, 5 pg, 1 pg, 0.5 pg, 0.1 pg) onto a nylon membrane (Biodyne B, Pall) and fixed by baking for 2 hours at 80° C. The membrane was prehybridized for 1.5 to 2 hours at 42° C. with ECL Gold Buffer (Amersham) or at 55° C. in Modified ECL Gold hybridization buffer (as described in Example 2). Both buffers were supplemented with 400 mM NaCl, 4% casein and 20 mM $MgCl_2$. The probe was prepared by cross-linking *R. marinus* alkaline phosphatase, Tth alkaline phosphatase, or Taq alkaline phosphatase to lambda DNA/Hind III fragments. Equal volumes (typically 10 µl each of heat denatured probe (10 ng/ml in water), alkaline phosphatase diluted immediately prior to use (40 ng/ml in 10 mM Na phosphate buffer pH 5.5) and formaldehyde (1.5% in water) were mixed and incubated at 37° C. for 30 minutes: The probe was added directly to the prehybridization reaction (5 ng/ml hybridization buffer) and allowed to hybridize overnight at 42° C. or 5520 C. Following hybridization, the membrane was washed as follows: one rinse and then 2×10 minute washes with the following buffer which is preheated to 55° C. (washing is done on a shaker platform at room temperature): 0.5× SSC, 0.1% SDS, 10 mM $MgCl_2$ 2M urea. Next, one rinse and then 2×5 minute washes with the following preheated to 55° C. (wash at RT ): 0.2× SSC, 10 mM $MgCl_2$. The final rinse is done at RT with 50 mM Tris pH 10, 100 mM NaCl, 2 mM $MgCl_2$ After washing, the membrane was placed in a sealed plastic bag with 20 µl CDP-star substrate (Tropix) per $cm^2$ membrane and exposed to autoradiography film for 3 hours.

Uses

Alkaline phosphatases of this invention have several potential uses in the numerous non-isotopic methods for the detection of proteins and nucleic acids. For example, the high pH optimum of this enzyme makes it suitable with dioxetane substrates which undergo rapid conversion to the luminescent form at alkaline pH. When using streptavidin conjugated alkaline phosphatase on positively charged membranes, as in nucleic acid hybridization, a pH greater than 9.5 is preferred to give decreased background. In addition, the high thermostability of this alkaline phosphatase makes it useful for direct crosslinking to nucleic acid probes. Hybridization and subsequent washes can be carried out under stringent conditions (i.e., elevated temperatures or in the presence of denaturants such as 6M urea) without loss of enzyme activity.

Alkaline phosphatases from different organisms may (or may not) behave similarly during purification. The high pH optimum for activity cannot be exploited for purification per se, but see below for screening. The high temperature optimum will be useful in purifying such enzymes after cloning into hosts that grow at a moderate temperature, such as *E. coli*. Extracts from *E. coli* could be heat treated to precipitate all proteins that denature at elevated temperatures.

If an enzyme is desired which is stable at 65°–75° C., it is possible to enhance the chances of discovery of such an enzyme by trying to isolate novel organisms that grow well at those temperatures. One could also select for organisms that are tolerant of high pH. In addition, knowing that an alkaline phosphatase is desired, one can then screen organisms, or libraries of recombinant clones, for alkaline phosphatase activity by use of the compound 5-bromo-4-chloro-3-indolyl phosphate (BCIP). A blue color is obtained when the phosphate group is removed from this compound, making it very convenient to screen for activity. A pH activity profile would then be prepared to determine whether the phosphate removing activity was an alkaline phosphatase.

Other embodiments are within the following claims.

We claim:

1. Method for detecting nucleic acid or protein in a sample comprising the step of providing a nucleic acid, protein, or antibody labeled with a thermostable alkaline phosphatase derived from *Rhodothermus marinus* which is stable to heating at 65° C. for 1 hour to said sample, and detecting said nucleic acid or protein in said sample utilizing said thermostable alkaline phosphatase.

2. Method for detecting nucleic acid or protein in a sample comprising the step of providing a nucleic acid, protein, or antibody labeled with a thermostable alkaline phosphatase present in *Thermosipho africanus* having a pH optimum greater than 10.5 and stable to heating at 65° C. for 1 hour to said sample, and detecting said nucleic acid or protein in said sample utilizing said thermostable alkaline phosphatase.

* * * * *

```
                          SEQUENCE LISTING (1) GENERAL INFORMATION:

(iii) NUMBER OF SEQUENCES:      7

(2) INFORMATION FOR SEQ ID NO:    1:

(i) SEQUENCE CHARACTERISTICS:
         (A) LENGTH:              2936 base pairs
         (B) TYPE:                nucleic acid
         (C) STRANDEDNESS:        single
         (D) TOPOLOGY:            linear (xi) SEQUENCE DESCRIPTION: SEQ ID NO: 1:

GGGTACCGGA GCGGCCGGGG TTGATGAGCG TGGCGAAGCG CTCGACGATC CGGCCGCCCT      60

GCACACGCAC GGCTGCCAGC TCGATGATCC GATCGGCAGG CCCGGAGCCC GTCGTCTCGG     120

TATCGACGAC GACGAACGAA ACGGCGTCGA GCTGCATCCC CTCAGTGGGC TTTCGCCGAC     180

GGCTTCCTCC CGCCGGAGGC CGTCTTCGGT CAGGGCTGGC AGGTCGAAAC CCATGAGCTT     240

CGGCCAGTAA GCTGACCGTA GTTCAGTCAT TCTCGAAGCT GCCCACCAGC CGATTCGGCG     300

GCACGGATCC GAAGGCGTAC AGATTGACGT CCACAGCGGT GTGGCCATTC GAGAGTCCAG     360

CCCACCACGG ACCCGGCGAC CGATCAGCTC GGTAACCACC TCGGCCCAGG TGTCGGGTTC     420

GGCCGTGGCC TGCGCGACGA GCGCCTGCTC GTCGGCGCGC AGGCTGTCGA GCCCGAGCCA     480

GGCCTGCAGG AGCGAGTCGG GTCGCTCCGA ACGGCGCAGT GCCGGGATAA GCCGTTCGTA     540

GGAAGCCTGC ACGCGGGCCA GCACTTCCGG GTGCCAGTCG TAGACGCCGC GGCCGTCCAC     600

GTTGCGCCCC AGCGACAGAC CGCCCGTCTC GTGGTCGGCC ACCGAGACGA CGAGCGTCTG     660

TCCGTCGCGG CGGGCAAAGT CGAGCGCCAC GGCCACGGCT TCATCGTAAG CCAGCACTTC     720

GCGGACGTGG GCGGCGGCGT CGTTGGCATG TCCGGCGTGG TCGATGCGGC TGCCCTCCAC     780

CATCAGGAAG AAGCCGTCCG GATCGTCCGC CAGCAGCTCG AGTGCCGCGC GGGTCATCTC     840

GGCCAGCGTA GGGGACCTCT TACCGGGTAC GACCGGTCAA TCTCGTAGGG CAGATGGCTT     900

GGCCCGAACA GTCCCAGCAC CGGTCTCCTC ACCCCCCGGC GGAAGTCGGC GGCCGTACGC     960

ACTACCTGGT AGCCCATCGC TTCGGCTTCG CGCAGCAGAT TGCGGCCGTC CTGTCTCCGT    1020

CCGCCCTCCG CGGTCGGCAG GAAATAGCTC CAGCCACCCC CCAGCAGCAC ATCGACGCGT    1080

TGCGCCAGCA TCTGCGCGGC GATTTCGCTT TCCATGCGCG CTGCGGCACA TGGGCGGCGA    1140

AGGCGGCCGG CGTGGCGTGT GAGATCCGGC TGGTCGCCAC CAGCCCGGTC GCCATCCCAC    1200

GCGCTTTTGC CGCTTCGAGC AACGTGGCGA GTGGGCGTCC GGCCGTATCG ACGGAATCGC    1260

GCCGTTGTAG GTCTTGACGC CGCAGGCATA GGCCGTCGCC CCGGCGAGCC GGAGTCGGTC    1320

ACCCGGCTGG AGGCCGAAGC AGTACGCACG GCACCGGTCT GAATGGCATC CAGCGTCAGT    1380

TCCTCACGTC CCAGCACGGC CCGGGCATAG TCACGGGCCA TCGTGATGCT GGCCGGACCA    1440

CACCCGTCGG CAATCATCAG GATCAGGTTC TTCGGACGCG GCGACTGGGC CCGAGCCCCT    1500

TCTCCGACCC CCAACAGCAT CACCAAAAAA CAGCAATATC CAGCGCATTG TCGATTCGCT    1560

CCCATCTTGA TGAACACGGG CTGTTCAAAG ATACGACAGA TCGGCTTTCA TCCACAGCGC    1620

CCGGATTATC TACGGAAAGA GCACCATAAA AAAGCCAACC ACCCGAACAC CTGTCCACCT    1680
```

-continued

```
TGAGGGCCAA CCCGGCCGGG TTGCGACCTC AACGCAGCAG GCCAAACAGG CCGCACAATC    1740

ACCCCGATCT GTCCGCCAGA AAATAAACAT CCAGCGCACC AGACTTGCAT ACCGCCGCTT    1800

AGCATCACTT TCACCTCGGC AATCCGGCTA TCAAGCTTCG CCTCCACCTC GGCAATCCGG    1860

CTGTCGAGCT TCGCCTCCAC TTCGGCGATC CGGCCGTCGA GCTTCGCTTC AACCTTGGAG    1920

ATCCGGCCAT TAAACTTTGC CTCTACCTCG GCAATTCGGC GGTCAAGCTT CACCTCTACG    1980

GCAGCGATGC GTTGTTCCAG ATGCGACACC TCCTACGCTG AATCCGACGG TCCACGCTTC    2040

GCCACCTCCT CCGTGATCGC GTCTGCTCCA GCACGCGCTT CCACCTCGGT GATGCGATTG    2100

TCCAGGCGCT TTTCGGTCTC GGCGACCCGC CGCGCGAAAC GCTCCTCTAC AATCCCCAGC    2160

AGATTGTTAC GCTCGTGATG GGCCGCCTCG TTGAGCAAAT TGATGAGCGC CTCGACACCT    2220

TCGTCGCCGA GCTTTTCACG CAAAGCTTTT CACGCAAAAC TTTCGGACGG TCAGATTGCC    2280

ATGAGCGCCT CCACATAGGA TAGGCTAAAA GGAAATCGCA CCTTATTTCT GGAGGTTCCC    2340

GTTTTCGTCC AAACCGTCCG GTGTCTCGTT GTCAATTGCC CGGCCAGGTT CGGAGGCTAG    2400

ATTCGAGCTG TCGGGCTAGC CAGGCGCCGT ATTGCGGATT GGGCAGGACG ATCCAGCGCG    2460

TGCCCCACCA GGAGCGATAA CGCCGGACCA GTGCTCGCCG TGCTTCGGCT CTGGTTTCAG    2520

GATCGACATA AAGTCGCCCA GCTGGTCGCC GATCTGGAGC AGGATGCGAT AGCGCTGGCC    2580

CAGGATACCC GGCGCGGTTC TTTGTCGGAA GATCCGCATT CGGGCCGCTC GCCACGCGTC    2640

AGGATTACGT CGAGCGTGTA CCGGCAGTGG GAAGCCGACG GCCTGCAGGT TACGACGGGT    2700

GGCCTCCTCC AGGTCGGCCG TGCGGTTGGT CACATAAAAG ACCTGACGCC GTGCCGGCGC    2760

GCCTCCTGTA CGAACACGAC AGCACCGGGC ACAGGTTCGG CCTGTGCAGC CTGCACCCAG    2820

CGCGCCCAGC TCTCCGGCGC AAAAGTCCGG CCCGTCGCAA CGAGCCAGGC CTGATAGGGG    2880

CTGTTGTCGA GCACGGTCTC GTCCACGTCC ACGATCCACT AGTTCTAGAG CGGCCG         2936
```

(2) INFORMATION FOR SEQ ID NO:    2:

(i) SEQUENCE CHARACTERISTICS:
        (A) LENGTH:           4454 base pairs
        (B) TYPE:             nucleic acid
        (C) STRANDEDNESS:     single
        (D) TOPOLOGY:         linear (xi) SEQUENCE DESCRIPTION: SEQ ID NO: 2:

```
TCGCGCGTTT CGGTGATGAC GGTGAAAACC TCTGACACAT GCAGCTCCCG GAGACGGTCA      60

CAGCTTGTCT GTAAGCGGAT GCCGGGAGCA GACAAGCCCG TCAGGGCGCG TCAGCGGGTG     120

TTGGCGGGTG TCGGGGCTGG CTTAACTATG CGGCATCAGA GCAGATTGTA CTGAGAGTGC     180

ACCATATGCG GTGTGAAATA CCGCACAGAT GCGTAAGGAG AAAATACCGC ATCAGGCGCC     240

ATTCGCCATT CAGGCTGCGC AACTGTTGGG AAGGGCGATC GGTGCGGGCC TCTTCGCTAT     300

TACGCCAGCT GGCGAAAGGG GGATGTGCTG CAAGGCGATT AAGTTGGGTA ACGCCAGGGT     360

TTTCCCAGTC ACGACGTTGT AAAACGACGG CCAGTGAATT CGAGCTCGGT ACCGAGCGGC     420

CGGGGTTGAT GAGCGTGGCG AAGCGCTCGA CGATCCGGCC GCCCTGCACA CGCACGGCTG     480

CCAGCTCGAT GATCCGATCG GCAGGCCCGG AGCCCGTCGT CTCGGTATCG ACGACGACGA     540

ACGAAACGGC GTCGAGCTGC ATCCCCTCAG TGGCTTTCGC CGACGGCTTC CTCCCGCCGG     600

AGCGTCTCGG TCAGGGCTGG CAGGTCGAAA CCCATGAGTT CGGCCAGTAA GCGGCCGAGT     660

TCGTCATTCT CGAAGCTGCC CACCAGCCGT TCGGCGCCGG GTCCGAAGGC GTACAGATTG     720

ACGTCCACAG CGGTGTGGCC ATTCGAGGTC CAGCCCACCA CGGCCCGGCG ACCGATCAGC     780
```

```
TCGGTAACCA CCTCGGCCCA GGTGTCGGGT TCGGCCGTGG CCTGCGCGAC GAGCGCCTGC    840
TCGTCGGCGC GCAGGCTGTC GAGCCCGAGC CAGGCCTGCA GGAGCGAGTC GGGTCGCTCC    900
GAACGGCGCA GTGCCGGGAT AAGCCGTTCG TAGGAAGCCT GCACGCGGGC CAGCACTTCC    960
GGGTGCCAGT CGTAGACGCC GCGGCCGTTC ACGTTGCGCC CCAGCGACAG ACCGCCCGTC   1020
TCGTGGTCGG CCACCGAGAC GACGAGCGTC TGTCCGTCGC GGCGGGCAAA GTCGAGCGCC   1080
ACGGCCACGG CTTCATCGTA AGCCAGCACT TCGCGGACGT GGGCGGCGGC GTCGTTGGCA   1140
TGTCCGGCGT GGTCGATGCG GCTGCCCTCC ACCATCAGGA GAAGCCGTC CGGATCGTCC    1200
GCCAGCAGCT CGAGTGCCGC GCGGGTCATC TCGGCCAGCG AGGGGACCTC TTCCGGGTCG   1260
CGGTCAATCT CGTAGGGCAG ATGGCTTGGC CCGAACAGTC CCAGCACCGG TCTCCTCACC   1320
CCCCGGCGGA AGTCGGCGGC CGTACGCACT ACCTGGTAGC CCATCGCTTC GGCTTCGCGC   1380
AGCAGATTGC GGCCGTCCTG TCTCCGTCCG CCCTCCGCGG TCGGCAGGAA ATAGCTCCAG   1440
CCACCCCCCA GCAGCACATG GACGCGTTGC GCCAGCATCT GCGCGGCGAT TTCGCTTTCC   1500
ATGGCGCGCT GCGGCACATG GGCGGCGAAG GCGGCCGGCG TGGCGTGTGA GATCCGGCTG   1560
GTCGCCACCA GCCCGGTCGC CATCCCACGC GCTTTTGCCG CTTCGAGCAA CGTGGCGAGT   1620
GGGCGTCCGG CCGTATCGAC GGCAATCGCG CCGTTGTAGG TCTTGACGCC GCAGGCATAG   1680
GCCGTCGCCC CGGCGGCCGA GTCGGTCACC CGGCTGGAGG CCGAAGCAGT ACGCACGGCA   1740
CCGGTCTGAA TGGCATCCAG CGTCAGTTCC TCACGTCCCA GCACGGCCCG GCATAGTCA   1800
CGGGCCATCG TGATGCTGGC CGGACCACAC CCGTCGGCAA TCATCAGGAT CAGGTTCTTC   1860
GGACGCGGCG ACTGGGCCCG AGCCCTTCT CCGACCCCCA ACAGCATCAC CAAAAACAGC    1920
AATATCCAGC GCATTGTGCA TCGCTCCATC TGATGAACAC GGGCTGTTCA AGATACGAC    1980
AGATCGGCTT TCATCCACAG CCCCGGATAC TACGGAAAGA GCACCATAAA AAAGCCAACC   2040
ACCCGAACAC CTGTCCACCT TGAGGGCCAA CCCGGCCGGG TTGCGACCTC AACGCAGCAG   2100
CGCAAACAGC GCCACAATCA CCCCGATCTG TCCCGCCCAG AAAATAAACA TCCAGCGCAC   2160
CAGACTTGCA TACCGCTCGC TTAGCATCAC TTTCACCTCG GCAATCCGGC TATCAAGCTT   2220
GGCGTAATCA TGGTCATAGC TGTTTCCTGT GTGAAATTGT TATCCGCTCA CAATTCCACA   2280
CAACATACGA GCCGGAAGCA TAAAGTGTAA AGCCTGGGGT GCCTAATGAG TGAGCTAACT   2340
CACATTAATT GCGTTGCGCT CACTGCCCGC TTTCCAGTCG GGAAACCTGT CGTGCCAGCT   2400
GCATTAATGA ATCGGCCAAC GCGCGGGGAG AGGCGGTTTG CGTATTGGGC GCTCTTCCGC   2460
TTCCTCGCTC ACTGACTCGC TGCGCTCGGT CGTTCGGCTG CGGCGAGCGG TATCAGCTCA   2520
CTCAAAGGCG GTAATACGGT TATCCACAGA ATCAGGGGAT AACGCAGGAA AGAACATGTG   2580
AGCAAAAGGC CAGCAAAAGG CCAGGAACCG TAAAAAGGCC GCGTTGCTGG CGTTTTTCCA   2640
TAGGCTCCGC CCCCCTGACG AGCATCACAA AAATCGACGC TCAAGTCAGA GGTGGCGAAA   2700
CCCGACAGGA CTATAAAGAT ACCAGGCGTT TCCCCCTGGA AGCTCCCTCG TGCGCTCTCC   2760
TGTTCCGACC CTGCCGCTTA CCGGATACCT GTCCGCCTTT CTCCCTTCGG GAAGCGTGGC   2820
GCTTTCTCAA TGCTCACGCT GTAGGTATCT CAGTTCGGTG TAGGTCGTTC GCTCCAAGCT   2880
GGGCTGTGTG CACGAACCCC CCGTTCAGCC CGACCGCTGC GCCTTATCCG GTAACTATCG   2940
TCTTGAGTCC AACCCGGTAA GACACGACTT ATCGCCACTG GCAGCAGCCA CTGGTAACAG   3000
GATTAGCAGA GCGAGGTATG TAGGCGGTGC TACAGAGTTC TTGAAGTGGT GGCCTAACTA   3060
CGGCTACACT AGAAGGACAG TATTTGGTAT CTGCGCTCTG CTGAAGCCAG TTACCTTCGG   3120
AAAAAGAGTT GGTAGCTCTT GATCCGGCAA ACAAACCACC GCTGGTAGCG GTGGTTTTTT   3180
```

```
TGTTTGCAAG CAGCAGATTA CGCGCAGAAA AAAAGGATCT CAAGAAGATC CTTTGATCTT     3240

TTCTACGGGG TCTGACGCTC AGTGGAACGA AAACTCACGT TAAGGGATTT TGGTCATGAG     3300

ATTATCAAAA AGGATCTTCA CCTAGATCCT TTTAAATTAA AAATGAAGTT TTAAATCAAT     3360

CTAAAGTATA TATGAGTAAA CTTGGTCTGA CAGTTACCAA TGCTTAATCA GTGAGGCACC     3420

TATCTCAGCG ATCTGTCTAT TTCGTTCATC CATAGTTGCC TGACTCCCCG TCGTGTAGAT     3480

AACTACGATA CGGGAGGGCT TACCATCTGG CCCCAGTGCT GCAATGATAC CGCGAGACCC     3540

ACGCTCACCG GCTCCAGATT TATCAGCAAT AAACCAGCCA GCCGGAAGGG CCGAGCGCAG     3600

AAGTGGTCCT GCAACTTTAT CCGCCTCCAT CCAGTCTATT AATTGTTGCC GGGAAGCTAG     3660

AGTAAGTAGT TCGCCAGTTA ATAGTTTGCG CAACGTTGTT GCCATTGCTA CAGGCATCGT     3720

GGTGTCACGC TCGTCGTTTG GTATGGCTTC ATTCAGCTCC GGTTCCCAAC GATCAAGGCG     3780

AGTTACATGA TCCCCCATGT TGTGCAAAAA AGCGGTTAGC TCCTTCGGTC CTCCGATCGT     3840

TGTCAGAAGT AAGTTGGCCG CAGTGTTATC ACTCATGGTT ATGGCAGCAC TGCATAATTC     3900

TCTTACTGTC ATGCCATCCG TAAGATGCTT TTCTGTGACT GGTGAGTACT CAACCAAGTC     3960

ATTCTGAGAA TAGTGTATGC GGCGACCGAG TTGCTCTTGC CCGGCGTCAA TACGGGATAA     4020

TACCGCGCCA CATAGCAGAA CTTTAAAAGT GCTCATCATT GGAAAACGTT CTTCGGGGCG     4080

AAAACTCTCA AGGATCTTAC CGCTGTTGAG ATCCAGTTCG ATGTAACCCA CTCGTGCACC     4140

CAACTGATCT TCAGCATCTT TTACTTTCAC CAGCGTTTCT GGGTGAGCAA AAACAGGAAG     4200

GCAAAATGCC GCAAAAAAGG GAATAAGGGC GACACGGAAA TGTTGAATAC TCATACTCTT     4260

CCTTTTTCAA TATTATTGAA GCATTTATCA GGGTTATTGT CTCATGAGCG GATACATATT     4320

TGAATGTATT TAGAAAAATA AACAAATAGG GGTTCCGCGC ACATTTCCCC GAAAAGTGCC     4380

ACCTGACGTC TAAGAAACCA TTATTATCAT GACATTAACC TATAAAAATA GGCGTATCAC     4440

GAGGCCCTTT CGTC                                                      4454

(2) INFORMATION FOR SEQ ID NO:    3:

(i) SEQUENCE CHARACTERISTICS:
           (A) LENGTH:        1368 base pairs
           (B) TYPE:          nucleic acid
           (C) STRANDEDNESS:  single
           (D) TOPOLOGY:      linear (xi) SEQUENCE DESCRIPTION: SEQ ID NO: 3:

ATGCGCTGGA TATTGCTGTT TTTGGTGATG CTGTTGGGGG TCGGAGAAGG GGCTCGGGCC      60

CAGTCGCCGC GTCCGAAGAA CCTGATCCTG ATGATTGCCG ACGGGTGTGG TCCGGCCAGC     120

ATCACGATGG CCCGTGACTA TGCCCGGGCC GTGCTGGGAC GTGAGGAACT GACGCTGGAT     180

GCCATTCAGA CCGGTGCCGT GCGTACTGCT TCGGCCTCCA GCCGGGTGAC CGACTCGGCC     240

GCCGGGGCGA CGGCCTATGC CTGCGGCGTC AAGACCTACA ACGGCGCGAT TGCCGTCGAT     300

ACGGCCGGAC GCCCACTCGC CACGTTGCTC GAAGCGGCAA AAGCGCGTGG GATGGCGACC     360

GGGCTGGTGG CGACCAGCCG GATCTCACAC GCCACGCCGG CCGCCTTCGC CGCCCATGTG     420

CCGCAGCGCG CCATGGAAAG CGAAATCGCC GCGCAGATGC TGGCGCAACG CGTCCATGTG     480

CTGCTGGGGG GTGGCTGGAG CTATTTCCTG CCGACCGCGG AGGGCGGACG GAGACAGGAC     540

GGCCGCAATC TGCTGCGCGA AGCCGAAGCG ATGGGCTACC AGGTAGTGCG TACGGCCGCC     600

GACTTCCGCC GGGGGGTGAG GAGACCGGTG CTGGGACTGT CGGGCCAAG CCATCTGCCC      660

TACGAGATTG ACCGCGACCC GGAAGAGGTC CCCTCGCTGG CCGAGATGAC CGCGCGGCA      720

CTCGAGCTGC TGGCGGACGA TCCGGACGGC TTCTTCCTGA TGGTGGAGGG CAGCCGCATC     780
```

```
GACCACGCCG GACATGCCAA CGACGCCGCC GCCCACGTCC GCGAAGTGCT GGCTTACGAT    840

GAAGCCGTGG CCGTGGCGCT CGACTTTGCC CGCCGCGACG GACAGACGCT CGTCGTCTCG    900

GTGGCCGACC ACGAGACGGG CGGTCTGTCG CTGGGGCGCA ACGTGAACGG CCGCGGCGTC    960

TACGACTGGC ACCCGGAAGT GCTGGCCCGC GTGCAGGCTT CCTACGAACG GCTTATCCCG   1020

GCACTGCGCC GTTCGGAGCG ACCCGACTCG CTCCTGCAGG CCTGGCTCGG GCTCGACAGC   1080

CTGCGCGCCG ACGAGCAGGC GCTCGTCGCG CAGGCCACGG CCGAACCCGA CACCTGGGCC   1140

GAGGTGGTTA CCGAGCTGAT CGGTCGCCGG GCCGTGGTGG GCTGGACCTC GAATGCCAC    1200

ACCGCTGTGG ACGTCAATCT GTACGCCTTC GGACCCGGCG CCGAACGGCT GGTGGGCAGC   1260

TTCGAGAATG ACGAACTCGG CCGCTTACTG GCCGAACTCA TGGGTTTCGA CCTGCCAGCC   1320

CTGACCGAGA CGCTCCGGCG GGAGGAAGCC GTCGGCGAAA GCCACTGA               1368
```

(2) INFORMATION FOR SEQ ID NO:    4:

(i) SEQUENCE CHARACTERISTICS:
     (A) LENGTH:           455 amino acids
     (B) TYPE:             amino acid
     (C) STRANDEDNESS:     single
     (D) TOPOLOGY:         linear (ii) MOLECULE TYPE:             peptide (xi) SEQUENCE DESCRIPTION: SEQ ID NO: 4:

```
Met Arg Trp Ile Leu Leu Phe Leu Val Met Leu Leu Gly Val Gly Glu
 1               5                  10                  15

Gly Ala Arg Ala Gln Ser Pro Arg Pro Lys Asn Leu Ile Leu Met Ile
             20                  25                  30

Ala Asp Gly Cys Gly Pro Ala Ser Ile Thr Met Ala Arg Asp Tyr Ala
         35                  40                  45

Arg Ala Val Leu Gly Arg Glu Glu Leu Thr Leu Asp Ala Ile Gln Thr
     50                  55                  60

Gly Ala Val Arg Thr Ala Ser Ala Ser Ser Arg Val Thr Asp Ser Ala
65                  70                  75                  80

Ala Gly Ala Thr Ala Tyr Ala Cys Gly Val Lys Thr Tyr Asn Gly Ala
                 85                  90                  95

Ile Ala Val Asp Thr Ala Gly Arg Pro Leu Ala Thr Leu Leu Glu Ala
            100                 105                 110

Ala Lys Ala Arg Gly Met Ala Thr Gly Leu Val Ala Thr Ser Arg Ile
        115                 120                 125

Ser His Ala Thr Pro Ala Ala Phe Ala Ala His Val Pro Gln Arg Ala
    130                 135                 140

Met Glu Ser Glu Ile Ala Ala Gln Met Leu Ala Gln Arg Val His Val
145                 150                 155                 160

Leu Leu Gly Gly Gly Trp Ser Tyr Phe Leu Pro Thr Ala Glu Gly Gly
                165                 170                 175

Arg Arg Gln Asp Gly Arg Asn Leu Leu Arg Glu Ala Glu Ala Met Gly
            180                 185                 190

Tyr Gln Val Val Arg Thr Ala Ala Asp Phe Arg Arg Gly Val Arg Arg
        195                 200                 205

Pro Val Leu Gly Leu Phe Gly Pro Ser His Leu Pro Tyr Glu Ile Asp
    210                 215                 220

Arg Asp Pro Glu Glu Val Pro Ser Leu Ala Glu Met Thr Arg Ala Ala
225                 230                 235                 240

Leu Glu Leu Leu Ala Asp Asp Pro Asp Gly Phe Phe Leu Met Val Glu
```

```
                       245                 250                 255
Gly Ser Arg Ile Asp His Ala Gly His Ala Asn Asp Ala Ala Ala His
                260                 265                 270
Val Arg Glu Val Leu Ala Tyr Asp Glu Ala Val Ala Val Ala Leu Asp
            275                 280                 285
Phe Ala Arg Arg Asp Gly Gln Thr Leu Val Val Ser Val Ala Asp His
        290                 295                 300
Glu Thr Gly Gly Leu Ser Leu Gly Arg Asn Val Asn Gly Arg Gly Val
305                 310                 315                 320
Tyr Asp Trp His Pro Glu Val Leu Ala Arg Val Gln Ala Ser Tyr Glu
                325                 330                 335
Arg Leu Ile Pro Ala Leu Arg Arg Ser Glu Arg Pro Asp Ser Leu Leu
                340                 345                 350
Gln Ala Trp Leu Gly Leu Asp Ser Leu Arg Ala Asp Glu Gln Ala Leu
            355                 360                 365
Val Ala Gln Ala Thr Ala Glu Pro Asp Thr Trp Ala Glu Val Val Thr
        370                 375                 380
Glu Leu Ile Gly Arg Arg Ala Val Val Gly Trp Thr Ser Asn Gly His
385                 390                 395                 400
Thr Ala Val Asp Val Asn Leu Tyr Ala Phe Gly Pro Gly Ala Glu Arg
                405                 410                 415
Leu Val Gly Ser Phe Glu Asn Asp Glu Leu Gly Arg Leu Leu Ala Glu
                420                 425                 430
Leu Met Gly Phe Asp Leu Pro Ala Leu Thr Glu Thr Leu Arg Arg Glu
            435                 440                 445
Glu Ala Val Gly Glu Ser His
450                 455

(2) INFORMATION FOR SEQ ID NO:    5:

(i) SEQUENCE CHARACTERISTICS:
        (A) LENGTH:         15 amino acids
        (B) TYPE:           amino acid
        (C) STRANDEDNESS:   single
        (D) TOPOLOGY:       linear (ii) MOLECULE TYPE:         peptide (ix) FEATURE:
        (D) OTHER INFORMATION:  Xaa stands for Ile or Lys.

(xi) SEQUENCE DESCRIPTION: SEQ ID NO: 5:

Val Lys Asn Val Ile Tyr Met Ile Gly Asp Gly Met Gly Xaa Asn
1               5                   10                  15

(2) INFORMATION FOR SEQ ID NO:    6:

(i) SEQUENCE CHARACTERISTICS:
        (A) LENGTH:         6 amino acids
        (B) TYPE:           amino acid
        (C) STRANDEDNESS:   single
        (D) TOPOLOGY:       linear (ii) MOLECULE TYPE:         peptide (ix) FEATURE:
        (D) OTHER INFORMATION:  Xaa stands for Val or Leu.

(xi) SEQUENCE DESCRIPTION: SEQ ID NO: 6:

Met Xaa Pro Val Leu Tyr
1               5
```

(2) INFORMATION FOR SEQ ID NO:    7:

(i) SEQUENCE CHARACTERISTICS:
        (A) LENGTH:            17 base pairs
        (B) TYPE:              nucleic acid
        (C) STRANDEDNESS:      single
        (D) TOPOLOGY:          linear (ix) FEATURE:
        (D) OTHER INFORMATION:    The letter "S" stands for G or C.
            The letter "B" stands for G, C or T.

(xi) SEQUENCE DESCRIPTION: SEQ ID NO:  7:

ATGSTSCCSG TSCTBTA                                      17